United States Patent [19]

Widdig et al.

[11] 4,261,988
[45] Apr. 14, 1981

[54] CHROMANONE DERIVATIVES

[75] Inventors: Arno Widdig, Odenthal; Hans-Joachim Kabbe, Leverkusen; Martin Scheer; Rüdiger Sitt, both of Wuppertal, all of Fed. Rep. of Germany

[73] Assignee: Bayer Aktiengesellschaft, Leverkusen, Fed. Rep. of Germany

[21] Appl. No.: 20,119

[22] Filed: Mar. 13, 1979

[30] Foreign Application Priority Data

Apr. 7, 1978 [DE] Fed. Rep. of Germany ....... 2814983

[51] Int. Cl.³ .................... A61K 31/35; C07D 311/22
[52] U.S. Cl. .............................. 424/244; 260/239 A; 260/239 E; 260/239 EP; 260/239 B; 260/239 BE; 260/239 BF; 260/326.36; 260/326.5 D; 260/326.5 SF; 260/333; 260/345.2; 424/267; 424/274; 424/275; 424/283; 546/17; 549/5; 549/6; 549/9; 549/13; 549/60
[58] Field of Search ................... 260/345.2, 326.5 D, 260/326.36, 326.5 SF, 333, 239 AR, 239 E, 239 EP, 239 B, 239 BE, 239 BF; 544/151; 546/207, 17; 424/283, 267, 274, 275, 244; 549/5, 13, 6, 9, 60

[56] References Cited

U.S. PATENT DOCUMENTS

| | | | |
|---|---|---|---|
| 3,410,851 | 11/1968 | Stauffer | 544/151 |
| 3,419,560 | 12/1968 | Bernstein et al. | 544/151 |
| 3,704,323 | 11/1972 | Krapcho | 260/345.2 |
| 3,753,985 | 8/1973 | Gavin et al. | 544/151 |
| 3,825,539 | 7/1974 | Freedman | 260/345.2 |

Primary Examiner—Nicky Chan

Attorney, Agent, or Firm—Sprung, Felfe, Horn, Lynch & Kramer

[57] ABSTRACT

Compounds useful in the treatment of cholesterolaemia are of the general formula

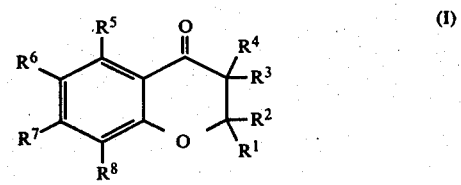

or salts thereof in which $R^1$ and $R^2$ independently denote radicals including hydrogen, alkyl, aryl and heterocyclic radical or together complete a carbocyclic or heterocylic ring, $R^3$ denotes a radical

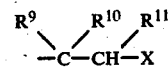

in which $R^9$, $R^{10}$ and $R^{11}$ include hydrogen, cyano, nitro, alkyl and aryl or, in pairs, complete carbocyclic rings, X denotes cyano, nitro or substituted carbonyl, sulphonyl or phosphonyl group, $R^4$ is hydrogen or a radical defined for $R^1$ or $R^3$, and $R^5$, $R^6$, $R^7$ and $R^8$ include hydrogen, nitro, cyano, carboxyl, alkyl and aryl or, in pairs, complete carbocyclic rings, with the proviso that $R^1$ and $R^9$ are not both phenyl if X denotes $CO-C_6H_6$. The compounds exhibit considerably higher hypocholesterolaemic activity than the known clofibrate and in addition exhibit a pronounced nutritive effect, e.g., in a medicated fodder or premix.

19 Claims, No Drawings

CHROMANONE DERIVATIVES

The present invention relates to new chromanone derivatives, to their production and to their use as additives for feed and as agents for the treatment of cholesterolaemia.

According to the present invention we provide compounds which are chromanone derivatives of the general formula

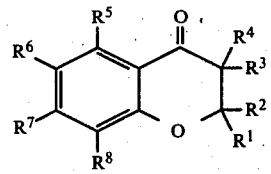

or a salt thereof, in which $R^1$ and $R^2$ are identical or different and denote a hydrogen atom or an optionally substituted alkyl, alkenyl, optionally substituted cycloalkyl, optionally substituted cycloalkenyl, optionally substituted aryl, optionally substituted aralkyl, alkoxycarbonyl, carboxyl, dialkylaminoalkyl or optionally substituted heterocyclic radical, or in which $R^1$ and $R^2$, together with the carbon atom between them, form an optionally substituted carbocyclic or optionally substituted heterocyclic ring, $R^3$ denotes a radical of the general formula

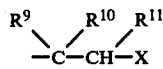

in which $R^9$, $R^{10}$ and $R^{11}$ are identical or different and denote a hydrogen atom or a cyano, nitro, optionally substituted alkyl, optionally substituted cycloalkyl, optionally substituted aryl, aralkyl, alkoxy, alkoxycarbonyl, optionally substituted aminocarbonyl or acyl group, or, $R^9$ and $R^{10}$, together with the carbon atom between them, form a carbocyclic ring, or $R^{10}$ and $R^{11}$, together with the carbon atoms between them, form a carbocyclic ring and X denotes a cyano or nitro group, or a radical of the general formula $COR^{12}$, $SO_2-R^{12}$ or $PO(R^{12})_2$, in which $R^{12}$ denotes a hydrogen atom or a hydroxyl, optionally substituted alkyl, optionally substituted aryl, aralkyl, alkoxy, aryloxy, alkenyloxy, aralkoxy, amino, alkylamino, alkenylamino, arylamino, dialkylamino, alkylarylamino or optionally substituted heterocyclic radical, $R^4$ denotes a hydrogen atom or denotes any of the radicals given for $R^1$ and $R^3$, and $R^5$, $R^6$, $R^7$ and $R^8$ are identical or different and denote a hydrogen or halogen atom or a hydroxyl, nitro, cyano, carboxyl, optionally substituted alkyl, optionally substituted cycloalkyl, optionally substituted aryl, aralkyl, alkoxy, aralkoxy, aryloxy, alkoxycarbonyl or dialkylamino group, or $R^5$ and $R^6$, together with the carbon atoms between them, form a carbocyclic ring, or $R^7$ and $R^8$, together with the carbon atoms between them, form a carbocyclic ring, or $R^9$ and $R^{12}$, together with the carbon atoms between them, form a carbocyclic ring, or $R^{11}$ and $R^{12}$, together with the carbon atoms between them, form a carbocyclic ring, with the proviso that $R^1$ and $R^9$ may not simultaneously denote phenyl if X denotes $CO-C_6H_5$.

Particularly preferred compounds of formula (I) are those in which $R^1$ and $R^2$ have the above mentioned meaning, $R^3$ denotes a radical of the general formula

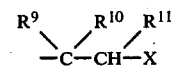

in which $R^9$, $R^{10}$ and $R^{11}$ are identical or different and denote a hydrogen atom or a $C_1$ to $C_4$ alkyl group, $R^4$ denotes a hydrogen atom or has the same meaning as $R^1$ or $R^3$, $R^5$, $R^6$, $R^7$ and $R^8$ are identical or different and denote a hydrogen or halogen atom or a $C_1$ to $C_4$ alkyl, hydroxyl, alkoxy, aryloxy or aralkoxy group and X denotes a cyano group or a radical of the general formula $COR^{12}$ or $SO_2R^{12}$, in which $R^{12}$ denotes a $C_1$ to $C_{12}$ alkyl, phenyl or naphthyl radical.

The present invention further relates to a process for the production of compounds of formula (I) comprising reacting a chromanone of the general formula

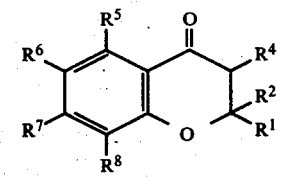

in which $R^1$, $R^2$, $R^4$, $R^5$, $R^6$, $R^7$ and $R^8$ have the meaning indicated above, with an olefine of the general formula

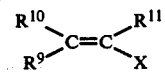

in which $R^9$, $R^{10}$, $R^{11}$ and X have the meaning indicated above, in the presence of a basic auxiliary and isolating the reaction products.

Surprisingly, the chromanone derivatives according to the invention exhibit a considerably higher hypocholesterolaemic activity than clofibrate, which is already known in the art. In addition, they exhibit a surprisingly highly pronounced nutritive effect, which has not hitherto been found in compounds of this class of substances.

If 2-spirocyclopenta-chroman-4-one and methyl vinyl ketone are used as starting materials, the course of the reaction can be represented by the equation which follows:

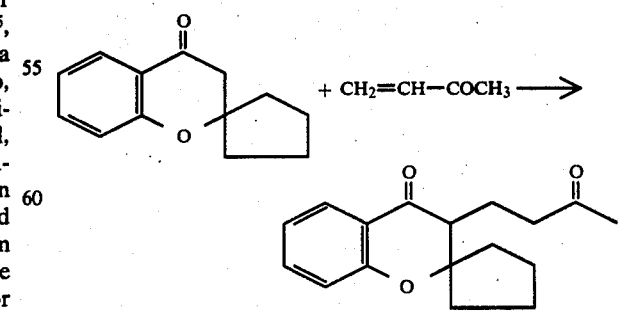

In the formulae (I), (II) and (III), optionally substituted alkyl $R^1$, $R^2$, $R^4$, $R^5$, $R^6$, $R^7$, $R^8$, $R^9$, $R^{10}$, $R^{11}$ and $R^{12}$ are straight-chain or branched alkyl radicals with up to 18, preferably up to 12 and particularly preferably up to 6, carbon atoms. Examples of alkyl radicals which may be mentioned are: methyl, ethyl, propyl, isopropyl, butyl, isobutyl, tert.-butyl, hexyl, 2-hexyl, 1,1-dimethylpentyl, 1,1-dimethylhexyl, 1,1-dimethylheptyl, nonyl, decyl, undecyl and octadecyl.

Alkenyl radicals $R^1$ and $R^2$ are straight-chain or branched alkenyl radicals with up to 18, preferably up to 12 and particularly preferably up to 6, carbon atoms. It is also possible for the alkenyl radicals to contain several double bonds to provide, for example, alkadienyl or alkatrienyl, etc. radicals. Examples which may be mentioned methylpent-3-enyl, 4,8-dimethylnona-3,7-dienyl and 4,8,12-trimethyltrideca-3,7,11-trienyl.

Possible optionally substituted cycloalkyl radicals $R^1$, $R^2$, $R^9$, $R^{10}$ and $R^{11}$ and $R^5$, $R^6$, $R^7$ and $R^8$ are preferably those with 3 to 18, preferably with 4 to 12 and particularly preferably with 5 or 6, carbon atoms, such as, for example, cyclopropyl, cyclobutyl, cyclopentyl, cyclohexyl, cycloheptyl, cyclooctyl, cyclododecyl, cycloheptadecyl and cyclooctadecyl, particularly preferably cyclopentyl and cyclohexyl.

Possible optionally substituted cycloalkenyl radicals $R^1$ and $R^2$ are preferably those with 3 to 18, preferably with 4 to 12 and particularly preferably with 5 and 6, carbon atoms, preferably 5- and 6-membered alicyclic radicals with a double bond, such as cyclopent-1-yl, cyclopent-2-enyl, cyclopent-3-enyl, cyclohex-1-enyl, cyclohex-2-enyl, cyclohex-3-enyl and 4-methylcyclohex-3-enyl.

Optionally substituted aryl $R^1$, $R^2$, $R^4$, $R^9$, $R^{10}$, $R^{11}$, $R^{12}$, $R^5$, $R^6$, $R^7$ and $R^8$ is aryl with preferably 6, or preferably 6 to 10, carbon atoms in the aryl part. Examples which may be mentioned are optionally substituted phenyl or naphthyl.

Possible optionally substituted aralkyl radicals $R^1$, $R^2$, $R^4$, $R^9$, $R^{10}$, $R^{11}$, $R^{12}$, $R^5$, $R^6$, $R^7$ and $R^8$ are preferably those with 7 to 18 carbon atoms, the aliphatic part of which contains 1 to 8, preferably 1 to 4, carbons and the aromatic part of which is a carbocyclic radical with 6 to 10 carbon atoms. The following aralkyl radicals may be mentioned as examples: benzyl, phenylethyl, phenylpropyl, phenylbutyl, naphthylmethyl and naphthylethyl, preferably benzyl.

Optionally substituted alkoxy $R^9$, $R^{10}$, $R^{11}$, $R^{12}$, $R^5$, $R^6$, $R^7$ and $R^8$ is straight-chain or branched alkoxy with preferably 1 to 6, in particular 1 to 4, carbon atoms. Examples which may be mentioned are optionally substituted methoxy, ethoxy, n- and i-propoxy and n-, i- and t-butoxy.

Optionally substituted alkoxycarbonyl $R^1$, $R^2$, $R^9$, $R^{10}$, $R^{11}$, $R^5$, $R^6$, $R^7$ and $R^8$ is straight-chain or branched alkoxycarbonyl with preferably 2 to 7, in particular 2 to 5, carbon atoms. Examples which may be mentioned are optionally substituted carbomethoxy, carboethoxy, carbo-n-and-i-propoxy and carbo-n-,-i- and-t-butoxy.

Preferred aryloxy groups $R^{12}$, $R^5$, $R^6$, $R^7$ and $R^8$ which may be mentioned are those with 6 or 10 carbon atoms, such as phenoxy and naphthoxy.

Preferred aralkoxy groups $R^{12}$, $R^5$, $R^6$, $R^7$ and $R^8$ which may be mentioned are those with 7 to 10 carbon atoms, such as benzyloxy, phenylethoxy, phenylpropoxy, phenylisopropoxy, phenylbutoxy, phenylisobutoxy and phenyl-tert.-butoxy.

Preferred alkylamino, alkenylamino, arylamino, aralkylamino and dialkylamino groups $R^{12}$, $R^5$, $R^6$, $R^7$ and $R^8$ which may be mentioned are those with up to 8 carbon atoms in the radical, such as, for example, methylamino, ethylamino, propylamino, isopropylamino, dimethylamino, diethylamino, dipropylamino, diisopropylamino, phenylethylamino, anilino, benzylamino, allylamino and diallylamino.

Halogens $R^5$, $R^6$, $R^7$ and $R^8$ which may be mentioned are fluorine, chlorine, bromine and iodine, preferably bromine and chlorine.

Acyl $R^9$, $R^{10}$ and $R^{11}$ is acyl, particularly alkanoyl with preferably 1 to 6, in particular 2 to 4 carbon atoms. Examples which may be mentioned are: formyl, acetyl, propionyl, n-butyryl and i-butyryl. In addition, acyl also preferably represents cycloalkylcarbonyl or arylcarbonyl, such as, for example, cyclohexylcarbonyl or benzoyl.

Dialkylaminoalkyl $R^1$ and $R^2$ is dialkylaminoalkyl with preferably 1 to 6, in particular 1 to 4, carbon atoms in each alkyl part. Examples which may be mentioned are N,N-dimethylaminomethyl, N,N-diethylaminomethyl, N,N-dimethylaminoethyl, N,N-diethylaminoethyl and N,N-methylethylaminomethyl.

Alkenyloxy radicals $R^{12}$ are alkenyloxy radicals with preferably 2 to 6, in particular 2 to 4, carbon atoms in the alkenyl part; examples which may be mentioned are: vinyloxy, allyloxy and methallyloxy.

Optionally substituted heterocyclic radicals $R^1$, $R^2$ and $R^{12}$ are hetero-paraffinic, hetero-aromatic and heteroolefinic 5-membered to 7-membered, preferably 5-membered or 6-membered, rings with preferably 1 to 3, in particular 1 or 2, identical or different hetero-atoms. Hetero-atoms are oxygen, sulphur or nitrogen. Examples which may be mentioned are optionally substituted pyrrolidinyl, piperidinyl, furyl, thienyl, pyrazolyl, imidazolyl, 1,2,3- and 1,2,4-triazolyl, oxazolyl, isoxazolyl, thiazolyl, isothiazolyl, 1,2,3-, 1,3,4-, 1,2,4- and 1,2,5-oxadiazolyl, azepinyl, pyrrolyl, isopyrrolyl, pyridyl, piperazinyl, pyridazinyl, pyrimidinyl, pyrazinyl, 1,3,5-, 1,2,4- and 1,2,3-triazinyl, oxepinyl, morpholinyl and thiepinyl.

If any of the substituent pairs $R^1$ and $R^2$, together with the carbon atom between them, $R^9$ and $R^{10}$, together with the carbon atom between them, $R^{10}$ and $R^{11}$, together with the carbon atoms between them, $R^5$ and $R^6$, together with the carbon atoms between them, or $R^7$ and $R^8$, together with the carbon atoms between them, form a carbocyclic ring, or if $R^9$ and $R^{12}$, together with the carbon atoms between them, form a carbocyclic ring, or if $R^{11}$ and $R^{12}$, together with the carbon atoms between them, form a carbocyclic ring, possible rings are saturated or unsaturated rings, preferably 3-membered to 12-membered rings, containing hydrocarbon members. It is also possible for the carbocyclic rings to be fused onto one or more radicals from the benzene series.

Examples of carbocyclic (preferably cycloalkyl) radicals which may be mentioned are: cyclopropane, cyclopentane, cyclohexane cycloheptane, cyclooctane, cyclononane, cyclodecane, cycloundecane, cyclododecane, cyclohexene, cyclooctene, cyclododecene and tetralin.

If any of the substituent pairs $R^1$ and $R^2$, together with the carbon atom between them, form an optionally substituted heterocyclic ring, possible rings are preferably 5-membered to 12-membered rings, in particular 5-membered and 6-membered rings, which, in addition to hydrocarbon members, also contain one or more hetero-atoms, such as, for example, nitrogen, oxygen and/or sulphur. The heterocyclic rings can contain 1 or 2 double bonds and can also be fused onto one or more radicals from the benzene series. Examples of heterocyclic radicals which may be mentioned are: piperidine, N-methyl- and N-benzylpiperidine, pyrrolidine, tetrahydrofurane, tetrahydropyrane and tetrahydrothiopyrane.

Possible substituents of the alkyl, cycloalkyl, cycloalkenyl, aryl, aralkyl, alkoxy and alkoxycarbonyl radicals of the substituents $R^1$, $R^2$, $R^4$, $R^9$, $R^{10}$, $R^{11}$, $R^{12}$, $R^5$, $R^6$, $R^7$ and $R^8$ are substituents which are not changed under the reaction conditions. Examples which may be mentioned are the halogens, such as fluorine, chlorine, bromine and iodine, the cyano group, the $C_1$-$C_6$-alkyl group, the $C_1$-$C_6$-alkoxy group, the $C_1$-$C_6$-alkoxycarbonyl group, the $C_1$-$C_6$-alkoxycarbonylalkyl group, the amino group, the $C_1$-$C_6$-alkylamino group and the $C_1$-$C_6$-dialkylamino group, aryl radicals from the benzene series or the carboxylic acid group.

As used herein, the terms such as aryl and aralkyl refer to substituents in which the aryl moiety is carbocyclic and is preferably mono- or bi-cyclic. Many of the chroman-4-ones of the formula II employed for the preparation of the compounds according to the invention are known (compare in this context the series Heterocyclic Compounds "Chromenes, Chromanones and Chromones", 207 et seq., Ed. G. P. Ellis, New York, London, Sydney, Toronto 1977 and German Offenlegungsschrift (German Published Specification) No. 2,611,910). Other chroman-4-ones of the formula II can be prepared by analogous processes.

Examples which may be mentioned of possible preparation processes for chroman-4-ones are:

(a) Condensation of o-hydroxyacetophenone with carbonyl compounds in the presence of basic condensation agents.

(b) Fries rearrangement of the phenol esters of $\alpha,\beta$-unsaturated carboxylic acids.

(c) Cyclisation of $\beta$-phenoxypropionic acids with acid condensation agents.

(d) Reduction of chromones.

Examples which may be mentioned of starting chromanones of the formula II are: chroman-4-one, 2-methylchroman-4-one, 6-chloro-chroman-4-one, 7-chloro-chroman-4-one, 6,8-dichloro-chroman-4-one, 6-methyl-chroman-4-one, 7-methyl-chroman-4-one, 6,7-dimethyl-chroman-4-one, 6,8-dimethyl-chroman-4-one, 6-methoxy-chroman-4-one, 7-methoxy-chroman-4-one, 6-ethoxy-chroman-4-one, 7-ethoxy-chroman-4-one, 6-chloro-2-methyl-chroman-4-one, 7-chloro-2-methyl-chroman-4-one, 2,6-dimethyl-chroman-4-one, 2,6,7-trimethylchroman-4-one, 6-methoxy-2-methyl-chroman-4-one, 7-methoxy-2-methyl-chroman-4-one, 6-chloro-2-ethyl-chroman-4-one, 7-chloro-2-ethyl-chroman-4-one, 6-methyl-2-ethyl-chroman-4-one, 2-ethyl-chroman-4-one, 2-propyl-chroman-4-one, 2-isopropyl-chroman-4-one, 2-butyl-chroman-4-one, 2-sec.-butyl-chroman-4-one, 2-tert.-butyl-chroman-4-one, 2,2-diethyl-chroman-4-one, 2,2-dimethyl-chroman-4-one, 2-methyl-2-propyl-chroman-4-one, 2-n-hexyl-chroman-4-one, 2-ethyl-7-methoxy-chroman-4-one, 7-methoxy-2-propyl-chroman-4-one, 2-isopropyl-7-methoxy-chroman-4-one, 2-butyl-7-methoxy-chroman-4-one, 2-sec.-butyl-7-methoxy-chroman-4-one, 2-tert.-butyl-7-methoxy-chroman-4-one, 2,2-diethyl-7-methoxy-chroman-4-one, 2,2-dimethyl-7-methoxy-chroman-4-one, 2-spirocyclopenta-chroman-4-one, 2-spirocyclohexa-chroman-4-one, 2-phenyl-chroman-4-one, 2-cyclohexyl-chroman-4-one, 2-benzyl-chroman-4-one, 2-phenylethyl-chroman-4-one, 2-phenylpropyl-chroman-4-one, 2-(4'-chlorophenyl)-chroman-4-one, 2-(4'-tolyl)-chroman-4-one, 2-($\beta$-dimethylaminoethyl)-chroman-4-one, 2-($\beta$-diethylaminoethyl)-chroman-4-one, 2-($\gamma$-dimethylaminopropyl)-chroman-4-one, 2-($\gamma$-diethylaminopropyl)-chroman-4-one, 2-($\beta$-N-pyrrolidinoethyl)-chroman-4-one, 2-($\beta$-N-morpholinoethyl)-chroman-4-one, 2-($\beta$-N-piperidinoethyl)-chroman-4-one, 2-($\gamma$-N-pyrrolidinopropyl)-chroman-4-one, 2-($\gamma$-N-morpholinopropyl)-chroman-4-one, 2-($\gamma$-N-piperidinopropyl)-chroman-4-one, 2-methyl-2-($\gamma$-diethylaminopropyl)-chroman-4-one, 2-methyl-2-($\gamma$-N-pyrrolidinopropyl)-chroman-4-one, 2-methyl-2-($\gamma$-N-morpholinopropyl)-chroman-4-one, 2-methyl-2-($\gamma$-N-piperidinopropyl)-chroman-4-one, 2-(4'-oxacyclohexyl)-chroman-4-one, 2-(4'-methylcyclohexyl)-chroman-4-one, 2-(2'-methylcyclohexyl)-chroman-4-one, 2-(4'-methyl-4'-azacyclohexyl)-chroman-4-one, 2-(4'-benzyl-4'-azacyclohexyl)-chroman-4-one, 2-)4'-phenyl-4'-azacyclohexyl)-chroman-4-one, 2-(4'-oxaspirocyclohexa)-chroman-4-one, 2-(4'-methyl-4'-azaspirocyclohexa)-chroman-4-one, 2-(4'-benzyl-4'-azaspirocyclohexa)-chroman-4-one, 2-(4'-phenyl-4'-azaspirocyclohexa)-chroman-4-one, 2-(cyclohex-3-enyl)-chroman-4-one, 6-chloro-2-spirocyclopenta-chroman-4-one, 7-chloro-2-spirocyclopenta-chroman-4-one, 6,8-dichloro-2-spirocyclopenta-chroman-4-one, 6-methyl-2-spirocyclopenta-chroman-4-one, 6-isopropyl-2-spirocyclopenta-chroman-4-one, 7-methyl-2-spirocyclopenta-chroman-4-one, 7-hydroxy-2-spirocyclopenta-chroman-4-one, 7-methoxy-2-spirocyclopenta-chroman-4-one, 7-isopropoxy-2-spirocyclopenta-chroman-4-one, 7-benzyloxy-2-spirocyclopenta-chroman-4-one, 7-phenyloxy-2-spirocyclopenta-chroman-4-one, 6,7-dimethyl-2-spirocyclopenta-chroman-4-one, 5-methoxy-2-spirocyclopenta-chroman-4-one, 5,6-benzo-2-spirocyclopenta-chroman-4-one, 7,8-benzo-2-spirocyclopenta-chroman-4-one, 7-phenyl-2-spirocyclopenta-chroman-4-one, 8-chloro-6-methylspirocyclopenta-chroman-4-one, 5,7-dihydroxy-2-spirocyclopenta-chroman-4-one, 6-chloro-2-spirocyclohexa-chroman-4-one, 7-chloro-2-spirocyclohexa-chroman-4-one, 6,8-dichloro-2-spirocyclohexa-chroman-4-one, 6-methyl-2-spirocyclohexa-chroman-4-one, 6-isopropyl-2-spirocyclohexa-chroman-4-one, 7-methyl-2-spirocyclohexa-chroman-4-one, 7-hydroxy-2-spirocyclohexa-chroman-4-one, 7-methoxy-2-spirocyclohexachroman-4-one, 7-isopropoxy-2-spirocyclohexa-chroman-4-one, 7-benzyloxy-2-spirocyclohexa-chroman-4-one, 7-phenyloxy-2-spirocyclohexa-chroman-4-one, 6,7-dimethyl-2-spirocyclohexa-chroman-4-one, 5-methoxy-2-spirocyclohexa-chroman-4-one, 5,6-benzo-2-spirocyclohexa-chroman-4-one, 7,8-benzo-2-spirocyclohexa-chroman-4-one, 7-phenyl-2-spirocyclohexa-chroman-4-one, 8-chloro-6-methyl-2-spirocyclohexa-chroman-4-one, 5,7-dihydroxy-2-spirocyclohexa-chroman-4-one, 2-isopropyl-3-phenyl-6-chlorochroman-4-one, 2-isopropyl-3-phenyl-7-methylchroman-4-one, 2-isopropyl-3-phenyl-7-methoxychroman-4-one and 2-isopropyl-3-p-methoxyphenyl-7-hydroxychroman-4-one.

The olefines of the formula (III) used for the preparation of the compounds I according to the invention are known; they are employed very frequently in industry and are accordingly copiously documented in the literature, compare, for example, Beilstein 1, 725 et seq.; 2, 397 et seq.; 4, 9 et seq.; 1 III 1,866 et seq. and so on.

Examples which may be mentioned of the olefines to be used according to the invention are: acrolein, crotonaldehyde, methacrolein, cinnamaldehyde, 4-chlorocinnamaldehyde, 4-methoxycinnamaldehyde, methyl vinyl ketone, ethyl vinyl ketone, methylisopropenyl ketone, mesityl oxide, 3-methyl-3-penten-2-one, 2-methyl-1-penten-3-one, 3-penten-2-one, 3-hepten-2-one, butyl vinyl ketone, n-amyl vinyl ketone, n-hexyl vinyl ketone, n-propyl vinyl ketone, phenyl vinyl ketone, 4-chlorophenyl vinyl ketone, 4-tolyl vinyl ketone, 4-methoxyphenyl vinyl ketone, benzylideneacetone, 2-chloro-benzylideneacetone, 4-chloro-benzylideneacetone, 4-methoxy-benzylideneacetone, 4-isopropyl-benzylideneacetone, ethylideneacetophenone, aethyl styryl ketone, isopropyl styryl ketone, benzylidenecyclohexanone, benzylidenecyclopentanone, 4-methoxybenzylidenecyclohexanone, 4-chlorobenzylidenecyclohexanone, benzylideneacetophenone, benzylidene-(4'-chloroacetophenone), benzylidene-(4'-methylacetophenone), benzylidene-(4'-methoxy-acetophenone), (4'-chlorobenzylidene)-acetophenone, (4-methylbenzylidene)-acetophenone, (4-methoxybenzylidene)-acetophenone, dibenzylideneacetone, cyclopent-2-en-1-one, cyclohex-2-en-1-one, 1-acetylcyclopentene, 1-acetylcyclohexene, 2-methylenecyclohexanone, 2-methylcyclohex-2-en-1-one, cyclopentylideneacetone, cyclohexylideneacetone, isophorone, carvone, 1-propionylcyclohexene, 1-butyrylcyclohexene, 1-benzoylcyclohexene, cyclohexylidenecyclohexanone, acrylonitrile, crotononitrile, methacrylonitrile, cyclopentylideneacetonitrile, vinyl β-methoxycarbonylethyl ketone, vinyl γvinyl γ-ethoxycarbonylpropyl ketone, cyclohexylideneacetonitrile, cinnamic acid nitrile, p-methoxycinnamic acid nitrile, 1-cyanocyclohexene, 1-cyanocyclopentene, acrylamide, methacrylamide crotonamide, acrylic acid dimethylamide, acrylic acid ethylamide, acrylic acid allylamide, acrylic acid tert.-butylamide, acrylic acid anilide, acrylic acid 4-ethoxyanilide, acrylic acid methyl ester, acrylic acid ethyl ester, acrylic acid cyclohexyl ester, acrylic acid benzyl ester, methacrylic acid methyl ester, crotonic acid methyl ester, acrylic acid, methacrylic acid, crotonic acid, ethylidenemalonic acid diethyl ester, dimethylmethylenemalonic acid diethyl ester, diethylmethylenemalonic acid diethyl ester, maleic acid diethyl ester, fumaric acid dimethyl ester, fumaric acid diethyl ester, ethylidenecyanoacetic acid ethyl ester, ethylidenecyanoacetic acid amide, cyclohexylidenecyanoacetic acid ethyl ester, ethylidenemalonodinitrile, cyclohexylidenemalonodinitrile, isobutylidenecyanoacetic acid ethyl ester, isobutylidenecyanoacetic acid amide, isobutylidenemalonodinitrile, cyclopent-1-ene-1-carboxylic acid ethyl ester, cyclohex-1-ene-1-carboxylic acid ethyl ester, cinnamic acid ethyl ester, cinnamic acid, cinnamic acid amide, cinnamic acid diethylamide, cinnamic acid anilide, 4-methoxycinnamic acid ethyl ester, 4-chlorocinnamic acid ethyl ester, benzylidenemalonic acid dimethyl ester, benzylidenemalonic acid diethyl ester, benzylidenecyanoacetic acid ethyl ester, benzylidenemalonodinitrile, benzylidenecyanoacetic acid amide, β-acetylacrylic acid ethyl ester, ethylideneacetoacetic acid ethyl ester, ethylideneacetoacetic acid amide, ethylideneacetoacetic acid anilide, β-benzoylacrylic acid ethyl ester, benzylideneacetoacetic acid ethyl ester, benzylideneacetoacetic acid amide, benzylideneacetoacetic acid anilide, benzylideneacetylacetone, ethylideneacetylacetone, 1-nitro-prop-1-ene, 2-nitro-prop-1-ene, 1-nitro-but-1-ene, 2-nitro-but-1-ene, ω-nitrostyrene, α-nitrostilbene, methyl vinyl sulphone, n-butyl vinyl sulphone, isobutyl vinyl sulphone, vinyl 4-tolyl sulphone, phenyl vinyl sulphone, phenyl styryl sulphone, vinylsulphonic acid amide, vinylsulphonic acid diethylamide, vinylsulphonic acid anilide, vinylsulphonic acid pyrrolidide, vinylsulphonic acid morpholide, vinylphosphonic acid diethyl ester and vinylsulphonic acid.

The basic auxiliaries used according to the invention are known. Examples which may be mentioned are alkali metal hydroxides, such as sodium hydroxide or potassium hydroxide, alkali metal hydrides, such as sodium hydride or potassium hydride, alkali metal alcoholates, such as sodium methylate, sodium ethylate, potassium methylate, potassium ethylate and potassium tert.-butylate, metallic sodium or potassium, alkali metal amides, such as sodium amide or potassium amide, ammonia and organic nitrogen bases, such as diethylamine, diisopropylamine, pyridine, pyrrolidine, piperidine, triethylamine, tributylamine, benzyltrimethylammonium hydroxide, 1,4-diazabicyclo[2,2,2]-octane, 1,8-diazabicyclo[5,4,0]-undec-7-ene and 1,5-diazabicyclo[4,3,0]-non-5-ene. The basic auxiliaries are preferably employed in catalytic amounts.

The reaction according to the invention can frequently advantageously be carried out without dilution. However, if one or other or both of the starting substances are solid materials with a relatively high melting point, it is advantageous to use solvents. Possible solvents are solvents which are stable towards bases and are inert in the reaction according to the invention, and preferred examples which may be mentioned are: alcohols, such as methanol, ethanol, isopropanol or tert.-butanol, ethers, such as diethyl ether, diisopropyl ether, tetrahydrofurane or dioxane, hydrocarbons, such as hexane, cyclohexane, benzene or toluene or mixtures of such solvents.

The reaction temperatures can be varied within a substantial range. In general, the reaction is carried out between about 0° and about 200° C., preferably between about 20° and about 170° C.

In carrying out the process according to the invention, 1 or 2 mols of olefine are preferably employed per one mol of chromanone. It is possible to exceed these amounts. The reaction products can be isolated by distillation, crystallisation, concentration and recrystallisation, or by chromatographic separation.

Specific examples of new active compounds which may be mentioned are: 3-(γ-oxopropyl)-2-spirocyclopenta-chroman-4-one, 3-(γ-oxopropyl)-2-spirocyclohexa-chroman-4-one, 3-(γ-oxobutyl)-2-spirocyclopenta-chroman-4-one, 3-(γ-oxobutyl)-2-spirocyclohexa-chroman-4-one, 3-(γ-oxobutyl)-2,2-dimethyl-chroman-4-one, 3-(γ-oxobutyl)-2-propyl-chroman-4-one, 3-(γ-oxobutyl)-2-isopropyl-chroman-4-one, 3-(γ-oxobutyl)-2,2-diethyl-chroman-4-one, 3-(γ-oxobutyl)-2-methyl-2-propyl-chroman-4-one, 3-(γ-oxobutyl)-2-phenyl-chroman-4-one, 3-(γ-oxobutyl)-2-cyclohexyl-chroman-4-one, 3-(γ-oxobutyl)-2-cyclohex-3-enyl-chroman-4-one, 3-(γ-oxobutyl)-2-benzyl-chroman-4-one, 3-(γ-oxobutyl)-2-phenylethyl-chroman-4-one, 3-(γ-oxobutyl)-2-β-phenylpropyl-chroman-4-one, 3-(γ-oxobutyl)-2-(4'-chlorophenyl)-chroman-4-one, 3-(γ-oxobutyl)-2-(4'-tolyl)-chroman-4-one, 3-(γ-oxobutyl)-2-(β-dimethylaminoethyl)-chroman-4-one, 3-(γ-oxobutyl)-2-(β-diethylaminoethyl)-chroman-4-one, 3-(γ-oxobutyl)-2-(γ-dimethylaminopropyl)-chroman-4-one, 3-(γ-oxobutyl)-2-(γ-diethylaminopropyl)-chroman-4-one, 3-(γ-oxobutyl)-2-(β-N-pyrrolidinoethyl)-chroman-4-one, 3-(γ-oxobutyl)-2-(β-N-morpholinoethyl)-chroman-4-one, 3-(γ-oxobutyl)-2-(β-N-piperidinoethyl)-chroman-4-one, 3-(γ-oxobutyl)-2-(γ-N-pyrrolidinopropyl)-chroman-4-one, 3-(γ-oxobutyl)-2-(γ-N-piperidinopropyl)-chroman-4-one, 3-(γ-oxobutyl)-2-(γ-N-morpholinopropyl)-chroman-4-one, 3-(γ-oxobutyl)-2-chroman-4-one, 3-(γ-oxobutyl)-2-methyl-chroman-4-one, 3-(γ-oxobutyl)-2-ethyl-chroman-4-one, 3-(γ-oxobutyl)-2-methoxycarbonyl-2-methyl-chroman-4-one, 3-(γ-oxobutyl)-2-methyl-2-(γ-diethylaminopropyl)-chroman-4-one, 3-(γ-oxobutyl)-2-methyl-2-(γ-N-pyrrolidinopropyl)-chroman-4-one, 3-(γ-oxobutyl)-2-methyl-2-(γ-N-morpholinopropyl)-chroman-4-one, 3-(γ-oxobutyl)-2-methyl-2-(γ-N-piperidinopropyl)-chroman-4-one, 3-(γ-oxobutyl)-2-(α'-oxacyclohexyl)-chroman-4-one, 3-(γ-oxobutyl)-2-(4'-methylcyclohexyl)-chroman-4-one, 3-(γ-oxobutyl)-2-(2'-methylcyclohexyl)-chroman-4-one, 3-(γ-oxobutyl)-2-(4'-methyl-4'-azacyclohexyl)-chroman-4-one, 3-(γ-oxobutyl)-2-(4'-benzyl-4'-azacyclohexyl)-chorman-4-one, 3-(γ-oxobutyl)-2-(4'-phenyl-4'-azacyclohexyl)-chroman-4-one, 3-(γ-oxobutyl)-2-(4'-oxaspirocyclohexa)-chroman-4-one, 3-(γ-oxobutyl)-2-(4'-methyl-4'-azaspirocyclohexa)-chroman-4-one, 3-(γ-oxobutyl)-2-(4'-benzyl-4'-azaspirocyclohexa)-chroman-4-one, 3-(γ-oxobutyl)-2-(4'-phenyl-4'-azaspirocyclohexa)-chroman-4-one, 3-(γ-oxobutyl)-2-butyl-chroman-4-one, 3-(γ-oxobutyl)-2-sec.-butyl-chroman-4-one, 3-(γ-oxobutyl)-2-isobutyl-chroman-4-one, 3-(γ-oxobutyl)-2-tert.-butyl-chroman-4-one, 3-(γ-oxobutyl)-2-[cyclohex-3-enyl]-chroman-4-one, 3-(γ-oxobutyl)-6-chloro-2-spirocyclopenta-chroman-4-one, 3-(γ-oxobutyl)-7-chloro-2-spirocyclopenta-chroman-4-one, 3-(γ-oxobutyl)-6,8-dichloro-2-spirocyclopenta-chroman-4-one, 3-(γ-oxobutyl)-6-methyl-2-spirocyclopenta-chroman-4-one, 3-(γ-oxobutyl)-6-isopropyl-2-spirocyclopenta-chroman-4-one, 3-(γ-oxobutyl)-7-methyl-2-spirocyclopenta-chroman-4-one, 3-(γ-oxobutyl)-7-hydroxy-2-spirocyclopenta-chroman-4-one, 3-(γ-oxobutyl)-7-methoxy-2-spirocyclopenta-chroman-4-one, 3-(γ-oxobutyl)-7-isopropoxy-2-spirocyclopenta-chroman-4-one, 3-(γ-oxobutyl)-7-benzyloxy-2-spirocyclopenta-chroman-4-one, 3-(γ-oxobutyl)-7-phenyloxy-2-spirocyclopenta-chroman-4-one, 3-(γ-oxobutyl)-6,7-dimethyl-2-spirocyclopenta-chroman-4-one, 3-(γ-oxobutyl)-5-methoxy-2-spirocyclopenta-chroman-4-one, 3-(γ-oxobutyl)-5,6-benzo-2-spirocyclopenta-chroman-4-one, 3-(γ-oxobutyl)-7,8-benzo-2-spirocyclopenta-chroman-4-one, 3-(γ-oxobutyl)-7-phenyl-2-spirocyclopenta-chroman-4-one, 3-(γ-oxobutyl)-8-chloro-6-methyl-2-spirocyclopenta-chroman-4-one, 3-(γ-oxobutyl)-5,7-dihydroxy-2-spirocyclopenta-chroman-4-one, 3-(γ-oxobutyl)-6-chloro-2-spirocyclohexa-chroman-4-one, 3-(γ-oxobutyl)-7-chloro-2-spirocyclohexa-chroman-4-one, 3-(65 -oxobutyl)-6,8-dichloro-2-spirocyclohexa-chroman-4-one, 3-(γ-oxobutyl)-6-methyl-2-spirocyclohexa-chroman-4-one, 3-(γ-oxobutyl)-6-isopropyl-2-spirocyclohexa-chroman-4-one, 3-(γ-oxobutyl-7-methyl-2-spirocyclohexa-chroman-4-one, 3-(γ-oxobutyl-7-hydroxy-2-spirocyclohexa-chroman-4-one, 3-(γ-oxobutyl-7-methoxy-2-spirocyclohexa-chroman-4-one, 3-(γ-oxobutyl-7-isopropoxy-2-spirocyclohexa-chroman-4-one, 3-(γ-oxobutyl-7-benzyloxy-2-spirocyclohexa-chroman-4-one, 3-(γ-oxobutyl-7-phenyloxy-2-spirocyclohexa-chroman-4-one, 3-(γ-oxobutyl-6,7-dimethyl-2-spirocyclohexa-chroman-4-one, 3-(γ-oxobutyl)-5-methoxy-2-spirocyclohexa-chroman-4-one, 3-(γ-oxobutyl)-5,6-benzo-2-spirocyclohexa-chroman-4-one, 3-(γ-oxobutyl-7,8-benzo-2-spirocyclohexa-chroman-4-one, 3-(γ-oxobutyl-7-phenyl-2-spirocyclohexa-chroman-4-one, 3-(γ-oxobutyl-8-chloro-6-methyl-2-spirocyclohexa-chroman-4-one, 3-(γ-oxobutyl-5,7-dihydroxy-2-spirocyclohexa-chroman-4-one, 3-(γ-oxobutyl-6-chloro-2,2-dimethyl-2-spirocyclohexa-chroman-4-one, 3-(γ-oxobutyl-2,2,6-trimethyl-2-spirocyclohexa-chroman-4-one, 3-(γ-oxobutyl-7-hydroxy-2-spirocyclohexa-chroman-4-one, 3-(γ-oxobutyl-7-methoxy-2-spirocyclohexa-chroman-4-one, 3-(γ-oxobutyl-5,6-benzo-2-spirocyclohexa-chroman-4-one, 3-(γ-oxobutyl-7,8-benzo-2-spirocyclohexa-chroman-4-one, 3-(γ-oxo-hexyl)-2-spirocyclopenta-chroman-4-one, 3-(γ-oxo-hexyl)-2-spirocyclohexa-chroman-4-one, 3-(γ-oxo-hexyl)-2,2-dimethyl-chroman-4-one, 3-(γ-oxo-hexyl)-2-phenyl-chroman-4-one, 3-(γ-oxo-hexyl)-2-cyclohexyl-chroman-4-one, 3-(γ-oxo-hexyl)-2-[cyclohex-3-enyl]-chroman-4-one, 3-(γ-oxo-hexyl)-2,2-diethyl-chroman-4-one, 3-(γ-oxo-hexyl)-2-propyl-chroman-4-one, 3-(γ-oxo-hexyl)-2-isopropyl-chroman-4-one, 3-(γ-oxo-hexyl)-2-hexyl-chroman-4-one, 3-(γ-oxo-nonyl)-2-spirocyclopenta-chroman-4-one, 3-(γ-oxo-nonyl)-2-spirocyclohexa-chroman-4-one, 3-(γ-oxo-nonyl)-2,2-dimethyl-chroman-4-one, 3-(γ-oxo-nonyl)-2-phenyl-chroman-4-one, 3-(γ-oxo-nonyl)-2-cyclohexyl-chroman-4-one, 3-(γ-oxo-nonyl)-2-(cyclohex-3'-enyl)-chroman-4-one, 3-(γ-oxo-nonyl)-2,2-diethyl-chroman-4-one, 3-(γ-oxo-nonyl)-2-propyl-chroman-4-one, 3-(γ-oxo-nonyl)-2-isopropyl-chroman-4-one, 3-(γ-oxo-nonyl)-2-hexyl-chroman-4-one, 3-(γ-oxo-γ-phenyl-propyl)-2-spirocyclopenta-chroman-4-one, 3-(γ-oxo-γ-phenylpropyl)-2-spirocyclohexa-chroman-4-one, 3-(γ-oxo-γ-phenylpropyl)-2,2-dimethyl-chroman-4-one, 3-(γ-oxo-γ-phenylpropyl)-2-phenyl-chroman-4-one, 3-(γ-oxo-γ-phenylpropyl)-2-cyclohexyl-chroman-4-one, 3-(γ-oxo-γ-phenylpropyl)-2-(cyclohex-3-enyl)-chroman-4-one, 3-(γ-oxo-γ-phenylpropyl)-2,2-diethyl-3-chroman-4-one, 3-(γ-oxo-γ-phenylpropyl)-2-propyl-3-chroman-4-one, 3-(γ-oxo-γ-phenylpropyl)-2-isopropyl-3-chroman-4-one, 3-(γ-oxo-γ-phenylpropyl)-2-hexyl-chroman-4-one, 3-(α-methyl-γ-oxobutyl)-2-spirocyclohexa-chroman-4-one, 3-(α-methyl-γ-oxobutyl)-2-spirocyclopenta-chroman-4-one, 3-(β-methyl-γ-oxobutyl)-2-spirocyclopenta-chroman-4-one, 3-(β-methyl-γ-oxobutyl)-2-spirocyclohexa-chroman-4-one, 3-(β-methyl-γ-oxobutyl)-2,2-dimethyl-chroman-4-one, 3-(β-methyl-γ-oxobutyl)-2-phenyl-chroman-4-one, 3-(β-methyl-γ-oxobutyl)-2-cyclohexyl-chroman-4-one, 3-(β-methyl-γ-oxobutyl)-2-isopropyl-chroman-4-one, 3-(β-methyl-γ-oxobutyl)-2-hexyl-chroman-4-one, 3-(α,α-dimethyl-γ-oxobutyl)-2-spirocyclopenta-chroman-4-one, 3-(α,α-dimethyl-γ-oxobutyl)-2-spirocyclohexa-chroman-4-one, 3-(α-phenyl-γ-oxobutyl)-2-spirocyclopenta-chroman-4-one, 3-[α-(4-chlorophenyl)-γ-oxobutyl]-2-spirocyclopenta-chroman-4-one, (3-[α-(4-chlorophenyl)-γ-oxobutyl]-2-spirocyclohexa-chroman-4-one, 3-[α-(4-totyl)-γ-oxobutyl]-2-spirocyclopenta-chroman-4-one, 3-[α-(4-tolyl)-γ-oxobutyl]-2-spirocyclohexa-chroman-4-one, 3-(α,γ-diphenyl-γ-oxobutyl)-2-spirocyclopenta-chroman-4-one, 3-(α,γ-diphenyl-γ-oxobutyl)-2-spirocyclohexa-chroman-4-one, 3-[α-(4-chlorophenyl)-γ-oxobutyl]-2-spirocyclopenta-chroman-4-one, 3-[α-(4-chlorophenyl)-γ-oxobutyl]-2-spirocyclohexa-chroman-4-one, 3-(α,α-tetramethylene-γ-oxobutyl)-2-spirocyclopenta-chroman-4-one, 3-(α,α-tetramethylene-γ-oxobutyl)-2-spirocyclohexa-chroman-4-one, 3-(α,α-pentamethylene-γ-oxobutyl)-2-spirocyclopenta-chroman-4-one, 3-(α,α-pentamethylene-γ-oxobutyl)-2-spirocyclohexa-chroman-4-one, 3-

(α,β-trimethylene-γ-oxobutyl)-2-spirocyclopenta-chroman-4-one, (3-(α,β-trimethylene-γ-oxobutyl)-2-spirocyclohexa-chroman-4-one, 3-(α,β-tetramethylene-γ-oxobutyl)-2-spirocyclopenta-chroman-4-one, 3-(α,β-tetramethylene-γ-oxobutyl)-2-spirocyclohexa-chroman-4-one, 3,3-di-(β-cyanoethyl)-2-spirocyclopenta-chroman-4-one, 3,3-di-(β-cyanoethyl)-2-spirocyclohexa-chroman-4-one, 3,3-di-(β-cyanoethyl)-2,2-dimethyl-chroman-4-one, 3,3-di-(β-cyanoethyl)-2-propyl-chroman-4-one, 3,3-di-(β-cyanoethyl)-2-isopropyl-chroman-4-one, 3,3-di-(β-cyanoethyl)-2,2-diethyl-chroman-4-one, 3,3-di-(β-cyanoethyl)-2-methyl-2-propyl-chroman-4-one, 3,3-di-(β-cyanoethyl)-2-phenyl-chroman-4-one, 3,3-di-(β-cyanoethyl)-2-cyclohexyl-chroman-4-one, 3,3-di-(β-cyanoethyl)-2-benzyl-chroman-4-one, 3,3-di-(β-cyanoethyl)-2-phenylethyl-chroman-4-one, 3,3-di-(β-cyanoethyl)-2-phenylpropyl-chroman-4-one, 3,3-di-(β-cyanoethyl)-2-(4'-chlorophenyl)-chroman-4-one, 3,3-di-(β-cyanoethyl)-2-(4'-tolyl)-chroman-4-one, 3,3-di-(β-cyanoethyl)-2-(β-dimethylaminoethyl)-chroman-4-one, 3,3-di-(β-cyanoethyl)-2-(β-diethylaminoethyl)-chroman-4-one, 3,3-di-(β-cyanoethyl)-2-(γ-dimethylaminopropyl)-chroman-4-one, 3,3-di-(β-cyanoethyl)-2-(γ-diethylaminopropyl)-chroman-4-one, 3,3-di-(β-cyanoethyl)-2-(β-N-pyrrolidinoethyl)-chroman-4-one, 3,3-di-(β-cyanoethyl)-2-(β-N-piperidinoethyl)-chroman-4-one, 3,3-di-(β-cyanoethyl)-2-(β-N-morpholinoethyl)-chroman-4-one, 3,3-di-(β-cyanoethyl)-2-(γ-N-pyrrolidinopropyl)-chroman-4-one, 3,3-di-(β-cyanoethyl)-2-(γ-N-piperidinopropyl)-chroman-4-one, 3,3-di-(β-cyanoethyl)-2-(γ-N-morpholinopropyl)-chroman-4-one, 3,3-di-(β-cyanoethyl)-chroman-4-one, 3,3-di-(β-cyanoethyl)-2-methyl-chroman-4-one, 3,3-di-(β-cyanoethyl)-2-ethyl-chroman-4-one, 3,3-di-(β-cyanoethyl)-2-methoxycarbonyl-2-methyl-chroman-4-one, 3,3-di-(β-cyanoethyl)-2-methyl-2-(γ-diethylaminopropyl)-chroman-4-one, 3,3-di-(β-cyanoethyl)-2-methyl-2-(γ-N-pyrrolidinopropyl)-chroman-4-one, 3,3-di-(β-cyanoethyl)-2-methyl-2-(γ-N-morpholinopropyl)-chroman-4-one, 3,3-di-(β-cyanoethyl)-2-methyl-2-(γ-N-piperidinopropyl)-chroman-4-one, 3,3-di-(β-cyanoethyl)-2-(4'-oxacyclohexyl)-chroman-4-one, 3,3-di-(β-cyanoethyl)-2-(4'-methylcyclohexyl)-chroman-4-one, 3,3-di-(β-cyanoethyl)-2-(2'-methylcyclohexyl)-chroman-4-one, 3,3-di-(β-cyanoethyl)-2-(4'-methyl-4'-azacyclohexyl)-chroman-4-one, 3,3-di-(β-cyanoethyl)-2-(4'-benzyl-4'-azacyclohexyl)-chroman-4-one, 3,3-di-(β-cyanoethyl)-2-(4'-phenyl-4'-azacyclohexyl)-chroman-4-one, 3,3-di-(β-cyanoethyl)-2-(4'-oxaspirocyclohexa)-chroman-4-one, 3,3-di-(β-cyanoethyl)-2-(4'-methyl-4'-azaspirocyclohexa)-chroman-4-one, 3,3-di-(β-cyanoethyl)-2-(4'-benzyl-4'-azaspirocyclohexa)-chroman-4-one, 3,3-di-(β-cyanoethyl)-2-(4'-phenyl-4'-azaspirocyclohexa)-chroman-4-one, 3,3-di-(β-cyanoethyl)-2-butyl-chroman-4-one, 3,3-di-(β-cyanoethyl)-2-sec.-butyl-chroman-4-one, 3,3-di-(β-cyanoethyl)-2-isobutyl-chroman-4-one, 3,3-di-(β-cyanoethyl)-2-tert.-butyl-chroman-4-one, 3,3-di-(β-cyanoethyl)-2-[cyclohex-3-enyl]-chroman-4-one, 3,3-di-(β-cyanoethyl)-6-chloro-2-spirocyclopenta-chroman-4-one, 3,3-di-(β-cyanoethyl)-7-chloro-2-spirocyclopenta-chroman-4-one, 3,3-di-(β-cyanoethyl)-6,8-dichloro-2-spirocyclopenta-chroman-4-one, 3,3-di-(β-cyanoethyl)-6-methyl-2-spirocyclopenta-chroman-4-one, 3,3-di-(β-cyanoethyl-6-isopropyl-2-spirocyclopenta-chroman-4-one, 3,3-di-(β-cyanoethyl)-7-methyl-2-spirocyclopenta-chroman-4-one, 3,3-di-(β-cyanoethyl)-7-hydroxy-2-spirocyclopenta-chroman-4-one, 3,3-di-(β-cyanoethyl)-7-methoxy-2-spirocyclopenta-chroman-4-one, 3,3-(β-cyanoethyl)-7-isopropoxy-2-spirocyclopenta-chroman-4-one, 3,3-di-(β-cyanoethyl)-7-benzyloxy-2-spirocyclopenta-chroman-4-one, 3,3-di-(β-cyanoethyl)-7-phenyloxy-2-spirocyclopenta-chroman-4-one, 3,3-di-(β-cyanoethyl)-6,7-dimethyl-2-spirocyclopenta-chroman-4-one, 3,3-di-(β-cyanoethyl)-5-methoxy-2-spirocyclopenta-chroman-4-one, 3,3-di-(β-cyanoethyl)-5,6-benzo-2-spirocyclopenta-chroman-4-one, 3,3-di-(β-cyanoethyl)-7,8-benzo-2-spirocyclopenta-chroman-4-one, 3,3-di-(β-cyanoethyl)-7-phenyl-2-spirocyclopenta-chroman-4-one, 3,3-di-(β-cyanoethyl)-8-chloro-6-methyl-2-spirocyclopenta-chroman-4-one, 3,3-di-(β-cyanoethyl)-5,7-dihydroxy-2-spirocyclopenta-chroman-4-one, 3,3-di-(β-cyanoethyl)-6-chloro-2-spirocyclohexa-chroman-4-one, 3,3-di-(β-cyanoethyl)-7-chloro-2-spirocyclohexa-chroman-4-one, 3,3-di-(β-cyanoethyl)-6,8-dichloro-2-spirocyclohexa-chroman-4-one, 3,3-di-(β-cyanoethyl)-6-methyl-2-spirocyclohexa-chroman-4-one, 3,3-di-(β-cyanoethyl)-6-isopropyl-2-spirocyclohexa-chroman-4-one, 3,3-di-(β-cyanoethyl)-7-methyl-2-spirocyclohexa-chroman-4-one, 3,3-di-(β-cyanoethyl)-7-hydroxy-2-spirocyclohexa-chroman-4-one, 3,3-di-(β-cyanoethyl)-7-methoxy-2-spirocyclohexa-chroman-4-one, 3,3-di-(β-cyanoethyl)-7-isopropoxy-2-spirocyclohexa-chroman-4-one, 3,3-di-(β-cyanoethyl)-7-benzyloxy-2-spirocyclohexa-chroman-4-one, 3,3-di-(β-cyanoethyl)-7-phenyloxy-2-spirocyclohexa-chroman-4-one, 3,3-di-(β-cyanoethyl)-6,7-dimethyl-2-spirocyclohexa-chroman-4-one, 3,3-di-(β-cyanoethyl)-5-methoxy-2-spirocyclohexa-chroman-4-one, 3,3-di-(β-cyanoethyl)-5,6-benzo-2-spirocyclohexa-chroman-4-one, 3,3-di-(β-cyanoethyl)-7,8-benzo-2-spirocyclohexa-chroman-4-one, 3,3-di-(β-cyanoethyl)-7-phenyl-2-spirocyclohexa-chroman-4-one, 3,3-di-(β-cyanoethyl)-8-chloro-6-methyl-2-spirocyclohexa-chroman-4-one, 3,3-di-(β-cyanoethyl)-5,7-dihydroxy-2-spirocyclohexa-chroman-4-one, 3,3-di-(β-cyanoethyl)-6-chloro-2,2-dimethyl-2-spirocyclohexa-chroman-4-one, 3,3-di-(β-cyanoethyl)-6-methyl-2-spirocyclohexa-chroman-4-one, 3,3-di-(β-cyanoethyl)-7-hydroxy-2-spirocyclohexa-chroman-4-one, 3,3-di-(β-cyanoethyl)-7-methoxy-2-spirocyclohexa-chroman-4-one, 3,3-di-(β-cyanoethyl)-5,6-benzo-2-spirocyclohexa-chroman-4-one, 3,3-di-(β-cyanoethyl)-7,8-benzo-2-spirocyclohexa-chroman-4-one, 3-(β-cyanoethyl)-2-spirocyclopenta-chroman-4-one, 3-(β-cyanoethyl)-2-spirocyclohexa-chroman-4-one, 3-(β-cyanoethyl)-2,2-dimethyl-chroman-4-one, 3-(β-cyanoethyl)-2-phenyl-chroman-4-one, 3-(β-cyanoethyl)-2-cyclohexyl-chroman-4-one, 3-(β-cyanoethyl)-2-[cyclohex-3-enyl]-chroman-4-one, 3-(β-cyanoethyl)-2,2-diethyl-chroman-4-one, 3-(β-cyanoethyl)-2-propyl-chroman-4-one, 3-(β-cyanoethyl)-2-isopropyl-chroman-4-one, 3-(β-cyanoethyl)-2-hexyl-chroman-4-one, 3-(β-cyanopropyl)-2-spirocyclopenta-chroman-4-one, 3-(β-cyanopropyl)-2-spirocyclohexa-chroman-4-one, 3-(β-cyanopropyl)-2,2-dimethyl-chroman-4-one, 3-(β-cyanopropyl)-2-phenyl-chroman-4-one, 3-(β-cyanopropyl)-2-cyclohexyl-chroman-4-one, 3-(β-cyanopropyl)-2-[cyclohex-3-enyl]-chroman-4-one, 3-(β-cyanopropyl)-2,2-diethyl-chroman-4-one, 3-(β-cyanopropyl)-2-propyl-chroman-4-one, 3-(β-cyanoethyl)-2-isopropyl-chroman-4-one, 3-(β-cyanoethyl)-2-hexyl-chroman-4-one, 3,3-di-(β-cyanopropyl)-2-spirocyclopenta-chroman-4-one, 3,3-di-(β-cyanopropyl)-2-spirocyclohexa-chroman-4-one, 3,3-di-(β-cyanopropyl)-2,2-dimethyl-chroman-4-one, 3,3-di-(β-cyanopropyl)-2-phenyl-chroman-4-one, 3,3-di-(β- cyanopropyl)-2-cyclohexyl-chroman-4-one, 3,3-di-(β-cyanopropyl)-2,2-diethyl-chroman-4-one, 3,3-di-(β-cyanopropyl)-2-propyl-chroman-4-one, 3,3-di-(β-cyanopropyl)-2-isopropyl-chroman-4-one, 3,3-di-(β-cyanopropyl)-2-hexyl-chroman-4-one, 3-(β-cyanoisopropyl)-2-spirocyclopenta-chroman-4-one, 3-(β-cyanoisopropyl)-2-spirocyclohexa-chroman-4-one, 3-(β-cyanoisopropyl)-2,2-dimethyl-chroman-4-one, 3-(β-cyanoisopropyl)-2-phenyl-chroman-4-one, 3-(β-cyanoisopropyl)-2-cyclohexyl-chroman-4-one, 3-(β-cyanoisopropyl)-2,2-diethyl-chroman-4-one, 3-(β-cyanoisopropyl)-2-propyl-chroman-4-one, 3-(β-cyanoisopropyl)-2-isopropyl-chroman-4-one, 3-(β-cyanoisopropyl)-2-hexyl-chroman-4-one, 3-(β-cyano-α-phenylethyl)-2-spirocyclopenta-chroman-4-one, 3-(β-cyano-α-phenylethyl)-2-spirocyclohexa-chroman-4-one, 3-(β-cyano-α-phenylethyl)-2,2-dimethyl-chroman-4-one, 3-(β-cyano-α-phenylethyl)-2-phenyl-chroman-4-one, 3-(β-cyano-α-phenylethyl)-2-cyclohexyl-chroman-4-one, 3-(β-cyano-α-phenylethyl)-2,2-diethyl-chroman-4-one, 3-(β-cyano-α-phenylethyl)-2-propyl-chroman-4-one, 3-(β-cyano-α-phenylethyl)-2-isopropyl-chroman-4-one, 3-(β-cyano-α-phenylethyl)-2-hexyl-chroman-4-one, 3-(β-methoxycarbonylethyl)-2-spirocyclopenta-chroman-4-one, 3-(β-methoxycarbonylethyl)-2-spirocyclohexa-chroman-4-one, 3-(β-methoxycarbonylethyl)-2-phenyl-chroman-4-one, 3-(β-methoxycarbonylethyl)-2-cyclohexyl-chroman-4-one, 3-(β-methoxycarbonylethyl)-2-[cyclohex-3-enyl]-chroman-4-one, 3-(β-methoxycarbonylethyl)-2,2-diethyl-chroman-4-one, 3-(β-methoxycarbonylethyl)-2-propyl-chroman-4-one, 3-(β-methoxycarbonylethyl)-2-isopropyl-chroman-4-one, 3-(β-methoxycarbonylethyl)-2-hexyl-chroman-4-one, 3-(β-ethoxycarbonylethyl)-2-spirocyclohexa-chroman-4-one, 3-(β-ethoxycarbonylethyl)-2-phenyl-chroman-4-one, 3-(β-allyloxycarbonylethyl)-2-phenyl-chroman-4-one, 3-(β-benzyloxycarbonylethyl)-2-isopropyl-chroman-4-one, 3-(β-methoxycarbonylpropyl)-2-spirocyclopenta-chroman-4-one, 3-(β-methoxycarbonylisopropyl)-2-cyclohexyl-chroman-4-one, 3,3-di-(β-methoxycarbonylethyl)-2-spirocyclopenta-chroman-4-one, 3,3-di-(β-methoxycarbonylethyl)-2-spirocyclohexa-chroman-4-one, 3,3-di-(β-methoxycarbonylethyl)-2-phenyl-chroman-4-one, 3,3-di-(β-methoxycarbonylethyl)-2-cyclohexyl-chroman-4-one, 3,3-di-(β-methoxycarbonylethyl)-2-propyl-chroman-4-one, 3,3-di-(β-methoxycarbonylethyl)-2-hexyl-chroman-4-one, 3-(β-aminocarbonyl-ethyl)-2-spirocyclopenta-chroman-4-one, 3-(β-aminocarbonyl-ethyl)-2-spirocyclohexa-chroman-4-one, 3-(β-aminocarbonyl-ethyl)-2,2-dimethyl-chroman-4-one, 3-(β-aminocarbonyl-ethyl)-2-phenyl-chroman-4-one, 3-(β-aminocarbonyl-ethyl)-2-cyclohexyl-chroman-4-one, 3-(β-aminocarbonyl-ethyl)-2-[cyclohex-3-enyl]-chroman-4-one, 3-(β-aminocarbonyl-ethyl)-2,2-diethyl-chroman-4-one, 3-(β-aminocarbonyl-ethyl)-2-propyl-chroman-4-one, 3-(β-aminocarbonyl-ethyl)-2-isopropyl-chroman-4-one, 3-(β-aminocarbonyl-ethyl)-2-hexyl-chroman-4-one, 3-(β-aminocarbonylpropyl)-2-spirocyclopenta-chroman-4-one, 3-(β-aminocarbonylpropyl)-2-phenyl-chroman-4-one, 3-(β-aminocarbonylpropyl)-2-isopropyl-chroman-4-one, 3-(β-aminocarbonylisopropyl)-2-spirocyclohexa-chroman-4-one, 3-(β-aminocarbonylisopropyl)-2-cyclohexyl-chroman-4-one, 3-(β-aminocarbonylisopropyl)-2-propyl-chroman-4-one, 3-(β-dimethylaminocarbonylethyl)-2-spirocyclopenta-chroman-4-one, 3-(β-dimethylaminocarbonylethyl)-2-phenyl-chroman-4-one, 3-(β-allylaminocarbonylethyl)-2-propyl-chroman-4-one, 3-(β-allylaminocarbonylethyl)-2-cyclohexyl-chroman-4-one, 3-(β-pyrrolidinocarbonylethyl)-2-spirocyclohexa-chroman-4-one, 3-(β-pyrrolidinocarbonylethyl)-2,2-dimethyl-chroman-4-one, 3-(tert.-butylaminocarbonylethyl)-2,2-diethyl-chroman-4-one, 3-(tert.-butylaminocarbonylethyl)-2-spirocyclopenta-chroman-4-one, 3-(β-piperidinocarbonylethyl)-2-methyl-chroman-4-one, 3-(β-phenylaminocarbonylethyl)-2-spirocyclopenta-chroma-4-one, 3-(β-N-methylphenylaminocarbonyl-ethyl)-2-spirocyclopenta-chroman-4-one, 3,3-di-(β-aminocarbonylethyl)-2-spirocyclopenta-chroman-4-one, 3,3-di-(β-aminocarbonylethyl)-2-spirocyclohexa-chroman-4-one, 3,3-di-(β-aminocarbonylethyl)-2-phenyl-chroman-4-one, 3,3-di-(β-aminocarbonylethyl)-2-benzyl-chroman-4-one, 3,3-di-(β-aminocarbonylethyl)-2,2-dimethyl-chroman-4-one, 3-(β-aminocarbonylpropyl)-2-spirocyclopenta-chroman-4-one, 3-(β-aminocarbonylpropyl)-2-phenyl-chroman-4-one, 3-(β-aminocarbonyl-isopropyl)-2-spirocyclohexa-chroman-4-one, 3-(β-aminocarbonyl-isopropyl)-2-cyclohexyl-chroman-4-one, 3-(βaminocarbonyl-α-phenylethyl)-2,2-dimethyl-chroman-4-one, 3-(β-aminocarbonyl-α-phenylethyl)-2,2-diethyl-chroman-4-one, 3-(β-nitro-α-phenylethyl)-2-spirocyclopenta-chroman-4-one, 3-(β-nitro-α-phenylethyl)-2-spirocyclohexa-chroman-4-one, 3-(β-nitro-α-phenylethyl)-2,2-dimethyl-chroman-4-one, 3-(β-nitro-α-phenylethyl)-2-phenyl-chroman-4-one, 3-(β-nitro-α-phenylethyl)-2-cyclohexyl-chroman-4-one, 3-(β-nitro-α-phenylethyl)-2-[cyclohex-3-enyl]-chroman-4-one, 3-(β-nitro-α-phenylethyl)-2,2-diethyl-chroman-4-one, 3-(β-nitro-α-phenylethyl)-2-propyl-chroman-4-one, 3-(β-nitro-α-phenylethyl)-2-isopropyl-chroman-4-one, 3-(β-nitro-α-phenylethyl)-2-hexyl-chroman-4-one, 3-(β-nitroisopropyl)-2-spirocyclopenta-chroman-4-one, 3-(β-nitroisopropyl)-2-phenyl-chroman-4-one, 3-(β-diethoxyphosphonylethyl)-2-spirocyclopenta-chroman-4-one, 3-(β-diethoxyphosphonylethyl)-2-spirocyclohexa-chroman-4-one, 3-(β-diethoxyphosphonylethyl)-2,2-dimethyl-chroman-4-one, 3-(β-diethoxyphosphonylethyl)-2-phenyl-chroman-4-one, 3-(β-diethoxyphosphonylethyl)-2-cyclohexyl-chroman-4-one, 3-(β-diethoxyphosphonylethyl)-2-isopropyl-chroman-4-one, 3-(β-diethoxyphosphonylethyl)-2-hexyl-chroman-4-one, 3-di-(β-methylsulphonyethyl)-2-spirocyclopenta-chroman-4-one, 3-di-(β-methylsulphonylethyl)-2-spirocyclohexa-chroman-4-one, 3-di-(β-methylsulphonylethyl)-2,2-dimethyl-chroman-4-one, 3-di-(β-methylsulphonylethyl)-2-propyl-chroman-4-one, 3-di-(β-methylsulphonylethyl)-2-isopropyl-chroman-4-one, 3-di-(β-methylsulphonylethyl)-2,2-diethyl-chroman-4-one, 3-di-(β-methylsulphonylethyl)-2-methyl-2-propyl-chroman-4-one, 3-di-(β-methylsulphonylethyl)-2-phenyl-chroman-4-one, 3-di-(β-methylsulphonylethyl)-2-cyclohexyl-chroman-4-one, 3-di-(β-methylsulphonylethyl)-2-benzyl-chroman-4-one, 3-di-(β-methylsulphonylethyl)-2-phenylethyl-chroman-4-one, 3-di-(β-methylsulphonylethyl)-2-phenylpropyl-chroman-4-one, 3-di-(β-methylsulphonylethyl)-2-(4'-chlorophenyl)-chroman-4-one, 3-di-(β-methylsulphonylethyl)-2-(4'-tolyl)-chroman-4-one, 3-di-(β-methylsulphonylethyl)-2-(β-dimethylaminoethyl)-chroman-4-one, 3-di-(β-methylsulphonylethyl)-2-(β-diethylaminoethyl)-chroman-4-one, 3-di-(β-methylsulphonylethyl)-2-(γ-dimethylaminopropyl)-chroman-4-one, 3-di-(β-methylsulphonylethyl)-2-(γ-diethylaminopropyl)-chroman-4-one, 3-di-(β-methylsulphonylethyl)-2-(β-N-pyrrolidinoethyl)-chroman-4-one, 3-di-(β-methylsulphonylethyl)-2-(β-N-piperidinoethyl)-chroman-4-one, 3-di-(β-,methylsulphonylethyl)-2-(β-N-morpholinoethyl)-chroman-4-one, 3-di-(β-methylsulphonylethyl)-2-methyl-2-(γ-diethylaminopropyl)-chroman-4-one, 3-di-(β-methylsulphonylethyl)-2-methyl-2-(γ-N-pyrrolidinopropyl)-chroman-4-one, 3-di-(β-methylsulphonylethyl)-2-methyl-2-(γ-N-piperidinopropyl)-chroman-4-one, 3-di-(β-methylsulphonylethyl)-2-methyl-2-(γ-N-morpholinopropyl)-chroman-4-one, 3-di-(β-methylsulphonylethyl)-chroman-4-one, 3-di-(β-methylsulphonylethyl)-2-methyl-chroman-4-one, 3-di-(β-methylsulphonylethyl)-2-ethyl-chroman-4-one, 3-di-(β-methylsulphonylethyl)-2-methoxycarbonyl-2-methylchroman-4-one, 3-di-(β-methylsulphonylethyl)-2-(4'-oxacyclohexyl)-chroman-4-one, 3-di-(β-methylsulphonylethyl)-2-(4'-methyl-cyclohexyl)-chroman-4-one, 3-di-(β-methylsulphonylethyl)-2-(2'-methyl-cyclohexyl)-chroman-4-one, 3-di-(β-methylsulphonylethyl)-2-(4'-methyl-4'-azacyclohexyl)-chroman-4-one, 3-di-(β-methylsulphonylethyl)-2-(4'-benzyl-4'-azacyclohexyl)-chroman-4-one, 3-di-(β-methylsulphonylethyl)-2-(4'-phenyl-4'-azacyclohexyl)-chroman-4-one, 3-di-(β-methylsulphonylethyl)-2-(4'-oxaspirocyclohexa)-chroman-4-one, 3-di-(β-methylsulphonylethyl)-2-(4'-methylspirocyclohexa)-chroman-4-one, 3-di-(β-methylsulphonylethyl)-2-(4'-methyl-4'-azaspirocyclohexa)-chroman-4-one, 3-di-(β-methylsulphonylethyl)-2-(4'-benzyl-4'-azaspirocyclohexa)-chroman-4-one, 3-di-(β-methylsulphonylethyl)-2-(4'-phenyl-4'-azaspirocyclohexa)-chroman-4-one, 3-di-(β-methylsulphonylethyl)-2-butyl-chroman-4-one, 3-di-(β-methylsulphonylethyl)-2-sec.-butyl-chroman-4-one, 3-di-(β-methylsulphonylethyl)-2-isobutyl-chroman-4-one, 3-di-(β-methylsulphonylethyl)-2-tert.-butyl-chroman-4-one, 3-di-(β-methylsulphonylethyl)-2-[cyclohex-3-yl]-chroman-4-one, 3-di-(β-methylsulphonylethyl)-6-chloro-2-spirocyclopenta-chroman-4-one, 3-di-(β-methylsulphonylethyl)-7-chloro-2-spirocyclopenta-chroman-4-one, 3-di-(β-methylsulphonylmethyl)-6,8-dichloro-2-spirocyclopenta-chroman-4-one, 3-di-(β-methylsulphonylmethyl)-6-methyl-2-spirocyclopenta-chroman-4-one, 3-di-(β-methylsulphonylmethyl)-6-isopropyl-2-spirocyclopenta-chroman-4-one, 3-di-(β-methylsulphonylmethyl)-7-methyl-2-spirocyclopenta-chroman-4-one, 3-di-(β-methylsulphonylmethyl)-7-hydroxy-2-spirocyclopenta-chroman-4-one, 3-di-(β-methylsulphonylmethyl)-7-methoxy-2-spirocyclopenta-chroman-4-one, 3-di-(β-methylsulphonylmethyl)-7-isopropoxy-2-spirocyclopenta-chroman-4-one, 3-di-(β-methylsulphonylmethyl)-7-benzyloxy-2-spirocyclopenta-chroman-4-one, 3-di-(β-methylsulphonylmethyl)-7-phenyloxy-2-spirocyclopenta-chroman-4-one, 3di-(β-methylsulphonylmethyl)-6,7-dimethyl-2-spirocyclopenta-chroman-4-one, 3-di-(β-methylsulphonylmethyl)-5-methoxy-2-spirocyclopenta-chroman-4-one, 3-di-(β-methylsulphonylmethyl)-5,6-benzo-2-spirocyclopenta-chroman-4-one, 3-di-(β-methylsulphonylmethyl)-7,8-benzo-2-spirocyclopenta-chroman-4-one, 3-di-(β-methylsulphonylmethyl)-7-phenyl-2-spirocyclopenta-chroman-4-one, 3-di-(β-methylsulphonylmethyl)-8-chloro-6-methyl-2-spirocyclopenta-chroman-4-one, 3-di-(β-methylsulphonylmethyl)-5,7-dihydroxy-2-spirocyclopenta-chroman-4-one, 3-di-(β-methylsulphonylmethyl)-6-chloro-2-spirocyclohexa-chroman-4-one, 3-di-(β-methylsulphonylmethyl)-7-chloro-2-spirocyclohexa-chroman-4-one, 3-di-(β-methylsulphonylmethyl)-6,8-dichloro-2-spirocyclohexa-chroman-4-one, 3-di-(β-methylsulphonylmethyl)-6-methyl-2-spirocyclohexa-chroman-4-one, 3-di-(β-methylsulphonylmethyl)-6-isopropyl-2-spirocyclohexa-chroman-4-one, 3-di-(β-methylsulphonylmethyl)-7-methyl-2-spirocyclohexa-chroman-4-one, 3-di-(β-methylsulphonylmethyl)-7-hydroxy-2-spirocyclohexa-chroman-4-one, 3-di-(β-methoxysulphonylethyl)-7-methoxy-2-spirocyclohexa-chroman-4-one, 3-di-(β-methylsulphonylethyl)-7-isopropyl-2-spirocyclohexa-chroman-4-one, 3-di-(β-methylsulphonylethyl)-7-benzyloxy-2-spirocyclohexa-chroman-4-one, 3-di-(β-methylsulphonylethyl)-7-phenyloxy-2-spirocyclohexa-chroman-4-one, 3-di-(β-methylsulphonylethyl)-6,7-dimethyl-2-spirocyclohexa-chroman-4-one, 3-di-(β-methylsulphonylethyl)-5-methoxy-2-spirocyclohexa-chroman-4-one, 3-di-(β-methylsulphonylethyl)-5,6-benzo-2-spirocyclohexa-chroman-4-one, 3-di-(β-methylsulphonylethyl)-7,8-benzo-2-spirocyclohexa-chroman-4-one, 3-di-(β-methylsulphonylethyl)-7phenyl 2-spirocyclohexa-chroman-4-one, 3-di-(β-methylsulphonylethyl)-8-chloro-6-methyl-2-spirocyclohexa-chroman-4-one, 3-di-(β-methylsulphonylethyl)-5,7-dihydroxy-2-spirocyclohexa-chroman-4-one, 3-di-(β-methylsulphonylethyl)-6-chloro-2,2-dimethyl-chroman-4-one, 3-di-(β-methylsulphonylethyl)-2,2,6-trimethyl-chroman-4-one, 3-di-(β-methylsulphonylethyl)-7-hydroxy-2,2-dimethyl-chroman-4-one, 3-di-(β-methylsulphonylethyl)-7-methoxy-chroman-4-one, 3-di-(β-methylsulphonylethyl)-5,6-benzo-chroman-4-one, 3-di-(β-methylsulphonylethyl)-7,8-benzo-chroman-4-one, 3-(β-phenylsulphonylethyl)-2-spirocyclopenta-chroman-4-one, 3-(β-phenylsulphonylethyl)-2-spirocyclohexa-chroman-4-one, 3-(β-phenylsulphonylethyl)-2,2-dimethyl-chroman-4-one, 3-di-(β-phenylsulphonylethyl)-2-propyl-chroman-4-one, 3-(β-phenylsulphonylethyl)-2-isopropyl-chroman-4-one, 3-(β-phenylsulphonylethyl)-2-cyclohexyl-chroman-4-one, 3-(β-phenylsulphonylethyl)-2-phenyl-chroman-4-one, 3-(β-dimethylaminosulphonylethyl)-2-spirocyclopenta-chroman-4-one, 3-(β-dimethylaminosulphonylethyl)-2-phenyl-chroman-4-one, 3-(β-pyrrolidinosulphonylethyl)-2-spirocyclohexa-chroman-4-one, 3-(β-pyrrolidinosulphonylethyl)-2-propyl-chroman-4-one, 3-(β-morpholinosulphonylethyl)-2-spirocyclopenta-chroman-4-one, 3-(β-morpholinosulphonylethyl)-2-hexyl-chroman-4-one, 3-(α-phenyl-β-pyrrolidinosulphonylethyl)-2-spirocyclopenta-chroman-4-one, 3-(α-phenyl-β-pyrrolidinosulphonylethyl)-2,2-dimethyl-chroman-4-one, 3-(α-phenyl-β-dimethylaminosulphonylethyl)-2-spirocyclohexa-chroman-4-one, 3-(α-phenyl-β-dimethylaminosulphonylethyl)-2-phenyl-chroman-4-one, 3-(β,β-dicyanoisopropyl)-2-spirocyclopenta-chroman-4-one, 3-(β,β-dicyanoisopropyl)-2,2-dimethyl-chroman-4-one, 3-(α-phenyl-β-ethoxycarbonyl-β-cyanoethyl)-2-phenyl-chroman-4-one, 3-(α-phenyl-β-ethoxycarbonyl-β-cyanoethyl)-2-hexyl-chroman-4-one, 3-(β-carboxamido-β-cyanoethyl)-2-spirocyclohexa-chroman-4-one, 3-(β-carboxamido-β-cyanoethyl)-2-propyl-chroman-4-one, 3-(α,β-dicyanoethyl)-2,2-diethyl-chroman-4-one, 3-(α,β-dicyanoethyl)-2-cyclohexyl-chroman-4-one, 3-(α,β-dimethoxycarbonylethyl)-2-methyl-2-propyl-chroman-4-one, 3-(α,β-dimethoxycarbonylethyl)-2-isopropyl-chroman-4-one, 3-(β-acetyl-β-ethoxycarbonylethyl)-2-spirocyclopenta-chroman-4-one and 3-(β-acetyl-β-ethoxycarbonylethyl)-2-phenyl-chroman-4-one.

Surprisingly, the chromanones of the formula (I) according to the invention have the property of promoting and accelerating growth in animals, so that these compounds can be used, for the purposes mentioned, in all areas of animal breeding and animal husbandry.

The activity of the compounds used according to the invention is largely independent of the species and sex of the animals. The chromanones of the formula (I) according to the invention prove particularly valuable in the rearing and keeping of young animals and fattening animals. The following stock animals and pets may be mentioned as examples of animals for which the compounds can be used for promoting and accelerating growth: warm-blooded animals, such as cattle, pigs, horses, sheep, goats, cats, dogs, rabbits, fur-bearing animals, for example mink and chinchillas, poultry, for example chicken, geese, ducks, turkeys and broilers, pigeons, parrots and canaries, and cold-blooded animals, such as fish, for example carp, and reptiles, for example snakes.

Chromanones of the formula (I) are preferably used in the rearing and keeping of ruminants, such as calves, goats and sheep, and for pigs and chicks.

The amount of chromanones of the formula (I) which is administered to the animals to achieve the desired effect can be varied substantially. It is preferably about 0.5 to 500, in particular 1 to 100, mg/kg of body weight daily. The period of administration can be from a few hours or days up to several years. The appropriate amount of active compound and the appropriate period of administration depend, in particular, on the species, age, sex, state of health and nature of keeping of the animals, and can easily be determined by any expert.

The compounds are administered to the animals by the customary methods. The nature of the administration depends, in particular, on the species, the behaviour and the state of health of the animals. Thus, administration can be effected orally or parenterally, once or several times daily at regular or irregular intervals. For reasons of expediency, in most cases oral administration, in particular in the rhythm of the intake of food and/or drink by the animals, is to be preferred.

The compounds can be administered as pure substances or in the formulated form, that is to say mixed with nontoxic inert carriers; by these there are to be understood solid, semi-solid or liquid diluents, fillers and formulation auxiliaries of all kinds.

Chromanones of the formula (I), optionally in the formulated form, can also be administered in a suitable form together with pharmaceutical active compounds, mineral salts, trace elements, vitamins, proteins, fats, colorants and/or flavouring agents.

Oral administration together with the feed and/or drinking water is recommended, the active compounds being added to the total amount or only portions of the feed and/or drinking water as required.

The compounds can be admixed to the feed and/or drinking water in accordance with customary methods by simple mixing as pure substances, preferably in the finely divided form or in the formulated form mixed with edible non-toxic carriers, and optionally also in the form of a premix or a feed concentrate.

The feed and/or drinking water can contain the active compound according to the invention in a concentration of, for example, about 5 to 500 ppm, in particular 5 to 50 ppm. The optimum level of the concentration of the active compound in the feed and/or drinking water depends, in particular, on the amount of feed and/or drinking water taken in by the animals and can easily be determined by any expert.

The nature of the feed and its composition is irrelevant. All the customary, commercially available or specific feed compositions, which preferably contain the customary equilibrium of energy substances and builder substances, including vitamines and mineral substances, necessary for balanced nutrition can be used. The feed can be composed, for example, of vegetable substances, for examply hay, beet, cereals and cereal by-products, animal substances, for example meat, fats and bone meal, fish products, vitamins, for example vitamin A, D complex and B complex, proteins, aminoacids, for example DL methionine, and inorganic substances, for example lime and sodium chloride.

Feed concentrates contain chromanones of the formula (I) alongside edible substances, for example rye flour, maize flour, soya bean flour or lime, optionally with further nutrients and builder substances, as well as proteins, mineral salts and vitamins. They can be prepared by the customary mixing methods.

In premixes and feed concentrates, preferably, the active compounds can optionally also be protected from air, light and/or moisture by suitable agents which coat their surfaces, for example with non-toxic waxes or gelatine.

The following is an example of the composition of a feed for rearing chicks, which contains chromanones of the formula (I): 200 g of wheat, 340 g of maize, 361 g of coarse soya bean meal, 60 g of beef tallow, 15 g of dicalcium phosphate, 10 g of calcium carbonate, 4 g of iodinated sodium chloride, 7.5 g of a vitamin/mineral mixture and 2.5 g of an active compound premix give, after careful mixing, 1 kg of feed.

The vitamin/mineral mixture consists of: 6,000 I.U. of vitamin A, 1,000 I.U. of vitamin $D_3$, 10 mg of vitamin E, 1 mg of vitamin $K_3$, 3 mg of riboflavin, 2 mg of pyridoxine, 20 mg of vitamin $B_{12}$, 5 mg of calcium pantothenate, 30 mg of nicotinic acid, 200 mg of choline chloride, 200 mg of $MnSO_4 \times H_2O$, 140 mg of $ZnSO_4 \times 7H_2O$, 100 mg of $FeSO_4 \times 7H_2O$ and 20 mg of $CuSO_4 \times 5H_2O$.

The active compound premix contains chromanones of the formula (I) in the desired amount, for example 100 mg, and also 1 g of DL-methionine as well as an amount of soya bean flour such that 2.5 g of premix are formed.

The following is an example of the composition of a feed for rearing pigs, which contains the active compounds according to the invention: 630 g of shredded cereal feed (composed of 200 g of maize, 150 g of shredded barley, 150 g of shredded oats and 130 g of shredded wheat), 80 g of fish meal, 60 g of coarse soya bean meal, 60 g of tapioca meal, 38 g of brewers' yeast, 50 g of a vitamin/mineral mixture for pigs (composition, for example, as for the chick feed), 30 g of linseed cake meal, 30 g of maize gluten feed, 10 g of soya bean oil, 10 g of sugar cane molasses and 2 g of an active compound premix (composition, for example, as for the chick feed) give, after careful mixing, 1 kg of feed.

The feed mixtures indicated are intended preferably for rearing and fattening chicks or pigs respectively, but they can also be used, in the same or a similar composition, for rearing and fattening other animals.

14-day feeding tests on chicks and 6-week feeding tests on broilers, which received 5 ppm to 50 ppm of a compound of the formula (I) with the feed, showed a significant increase in weight in the animals treated with the chromamones of the formula (I) in comparison with animals fed without the addition of chromanones of the formula (I).

Accordingly the present invention also relates to a medicated fodder comprising compounds of the invention and a nutritious material.

As stated above, the invention also relates to the use in medicine of the compounds of the invention.

The present invention provides pharmaceutical compositions containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides pharmaceutical compositions containing as active ingredient in compound of the invention in the form of a sterile and/or physiologically isotonic aqueous solution.

The invention also provides a medicaments in the unit form comprising a compound of the invention.

The invention also provides medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or sub-multiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical compositions according to the invention may, for example, take the form of suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are powders and sprays can, for example, contain the usual diluents, e.g. lactose, talc, silicic acid, aluminium hydroxide, calcium silicate, and polyamide powder or mixtures of these substances. Aerosol sprays can, for example, contain the usual propellants, e.g. chlorofluorohydrocarbons.

The pharmaceutical compositions which are solutions andd emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters or sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite an sorbitane esters), microcrystalline cellulose, aluminum metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.1 to 99.5%, usually from 0.5 to 95% of the active ingredient by weight of the total composition.

In addition to a compound of the invention, the pharmaceutical compositions and medicaments according to the invention can also contain other pharmaceuticall active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The production of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating the above-mentioned diseases in warm-blooded animals which comprises administering to the said animals a compound of the invention alone or in admixture with a diluent or in the form of a medicament according to the invention.

It is envisaged that these active compounds will be administered perorally, parenterally (for example intramuscularly, intraperitoneally, subcutaneously and intravenously), rectally or locally, preferably orally. Preferred pharmaceutical compositions and medicaments are therefore those adapted for administration such as oral administration. Administration in the method of the invention is preferably oral administration.

In general it has proved advantageous to administer amounts of from 0.05 mg to 500 mg/kg, preferably 0.5 mg to to 200 mg/kg, of body weight per day divided into 1 to 6 administrations, in particular before and/or during or/and after meals, to achieve effective results. An individual administration preferably contains the active compound or compounds in amounts of 0.1 to 100 mg/kg of body weight. Nevertheless, it can at times be necessary to deviate from those dosage rates, and in particular to do so as a function of the nature and body weight of the human or animal subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of the day.

The following Examples illustrate the preparation of individual compounds of the invention.

EXAMPLE 1

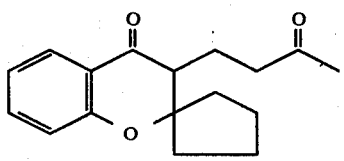

2-Spirocyclopenta-3-(γ-oxobutyl)-chroman-4-one 1,616 g (8 mols) of 2-spirocyclopenta-chroman-4-one are initially introduced into the reaction vessel together with a mixture of 22 ccs of 1,5-diazabicyclo[4,3,0]-non-5-ene in 100 ccs of absolute alcohol. 1,230 g (17.6 mols) of methyl vinyl ketone are then slowly added dropwise, whilst stirring and cooling moderately with ice. The mixture is kept at 30° C. and subsequently stirred for a further 6 hours, whilst cooling, and left to stand overnight. Thereafter, it is stirred with the same volume of methylene chloride, and the mixture is washed first with 5% strength acetic acid, then with bicarbonate solution and finally with water. After drying with sodium sulphate and concentrating, the mixture is distilled and rectified again. 927 g (42.7% of theory) of a pale-coloured oil of boiling point 158–167/0.15 are obtained.

EXAMPLE 2

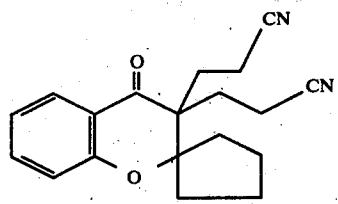

2-Spirocyclopenta-3,3-bis-(2-cyanoethyl)-chroman-4-one 202 g (1 mol) of 2-spirocyclopenta-chroman-4-one are initially introduced into the reaction vessel together with 0.8 g of sodium in 15 ml of alcohol. 159 g (3 mols) of freshly distilled acrylonitrile are added dropwise at 30°–50° C. After the slightly exothermic reaction has subsided, the mixture is stirred for a further hour. After cooling, the mixture is triturated thoroughly with a little methanol, whereupon crystallisation starts. Filtering off the crystals and washing them with methanol gives 222 g (72% of theory). After recrystallisation from alcohol, the substance, which consists of white crystals, melts at 84°–85° C.

EXAMPLE 3

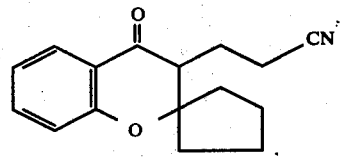

2-Spirocyclopenta-3-(2-cyanoethyl)-chroman-4-one 40.4 g (0.2 mol) of 2-spirocyclopenta-chroman-4-one are initially introduced into the reaction vessel together with a solution of 0.5 g of sodium in 2.5 ccs of alcohol. 15.9 g of acrylonitrile are added dropwise at 15°, whilst cooling, and the mixture is subsequently stirred for 2 hours, whilst further cooling. The compound, which is isolated in an amount of 8 g (15% of theory) by column chromatography over silica gel with toluene/methanol 100:5 and consists of white crystals, melts at 60°–62° C.

EXAMPLE 4

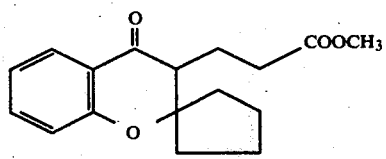

2-Spirocyclopenta-3-(2-carbomethoxyethyl)-chroman-4-one 1.5 g of sodium hydride are added to 202 g (1 mol) of 2-spirocyciopenta-chroman-4-one. 215 g (2.5 mols) of acrylic acid methyl ester are added dropwise at 30°–50° C. The mixture is then boiled for 16 hours and, after cooling, is stirred with the same volume of methylene chloride, and washed with 5% strength acetic acid, bicarbonate solution and water, dried over sodium sulphate and concentrated. Distillation under a high vacuum gives 130 g (45% of theory) of pale-coloured oil of boiling point 156°/0.1.

EXAMPLE 5

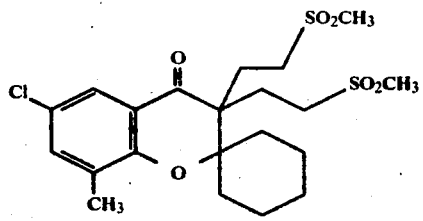

2-Spirocyclohexa-3,3-bis-(2-methylsulphonylethyl)-6-chloro-8-methyl-chroman-4-one 42.4 g (0.4 mol) of vinyl methyl sulphone are added to 49.3 g (0.2 mol) of 2-spirocyclohexa-6-chloro-8-methyl-chroman-4-one and 0.3 g of sodium in 50 ccs of alcohol and the mixture is heated to the boil for 2 hours. After cooling, the crystals which have precipitated are filtered off and washed with ether. 55 g (60% of theory) of white crystals are obtained. The melting point after recrystallisation from acetonitrile is 209°–10°.

The following compounds were prepared according to the process in Examples 1–5.

| Example | | |
|---|---|---|
| (6) | [structure] | Boiling point 155–60°/0.2 |
| (7) | [structure] | Boiling point 160–5°/0.2 |
| (8) | [structure] | Boiling point 155–61/0.2 |
| (9) | [structure] | Boiling point 170–5°/0.1 |
| (10) | [structure] | Boiling point 160–5°/0.2 |
| (11) | [structure] | Boiling point 120–5/0.2 |
| (12) | [structure] | Boiling point 135–40°/0.1 |

-continued
| Example | | |
|---|---|---|
| (13) | 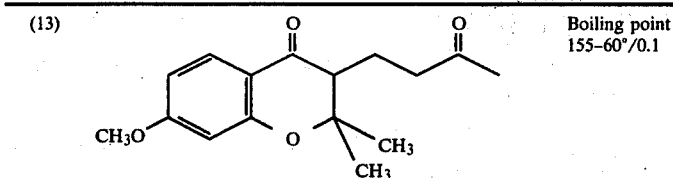 | Boiling point 155–60°/0.1 |
| (14) | 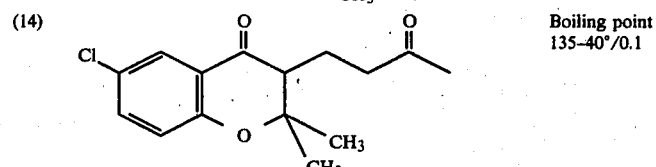 | Boiling point 135–40°/0.1 |
| (15) | 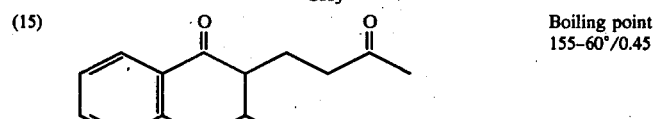 | Boiling point 155–60°/0.45 |
| (16) | 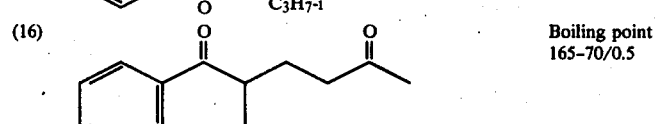 | Boiling point 165–70/0.5 |
| (17) | 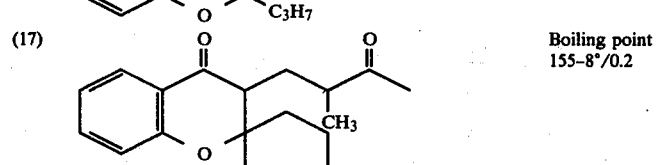 | Boiling point 155–8°/0.2 |
| (18) | 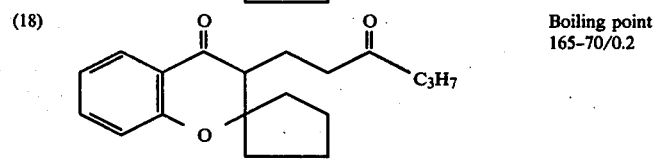 | Boiling point 165–70/0.2 |
| (19) | 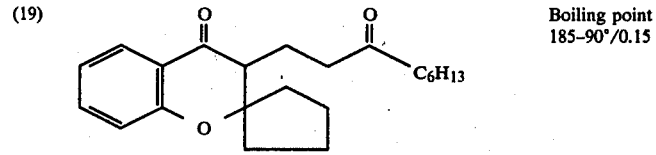 | Boiling point 185–90°/0.15 |
| (20) | 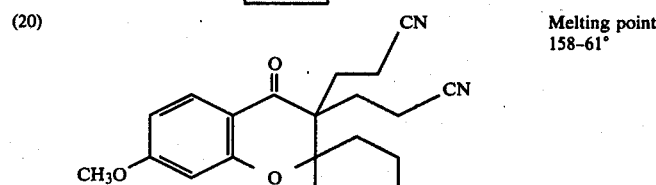 | Melting point 158–61° |
| (21) | 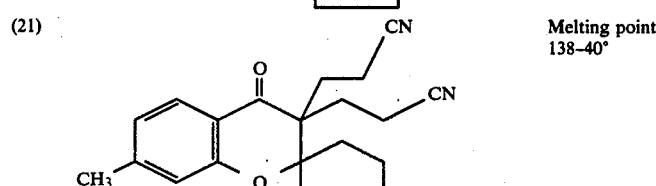 | Melting point 138–40° |
| (22) | 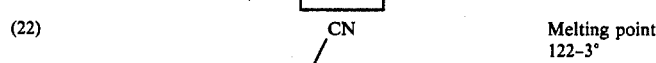 | Melting point 122–3° |

-continued
| Example | | |
|---|---|---|
| (23) | 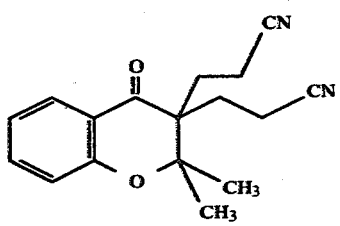 | Melting point 122–3° |
| (24) | 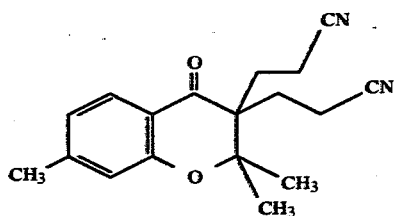 | Melting point 115–6° |
| (25) | 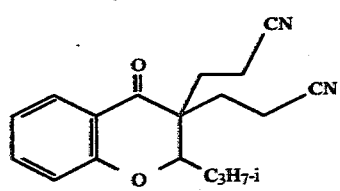 | Melting point 128–9° |
| (26) | 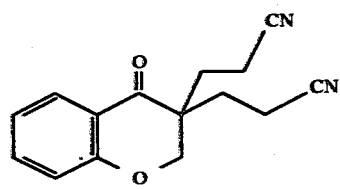 | Melting point 81–3° |
| (27) | 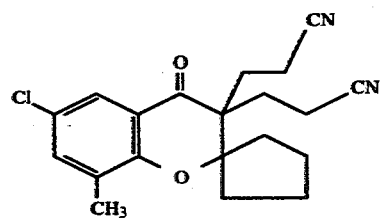 | Melting point 104–6° |
| (28) | 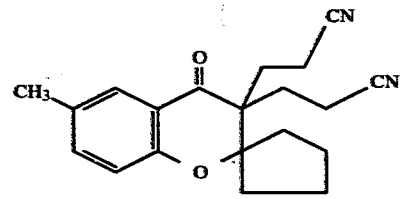 | Melting point 87–8° |
| (29) | 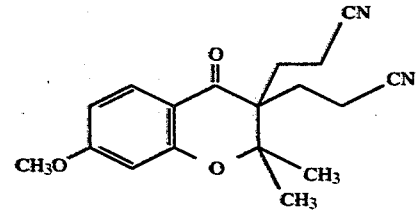 | Melting point 121–2° |
| (30) | 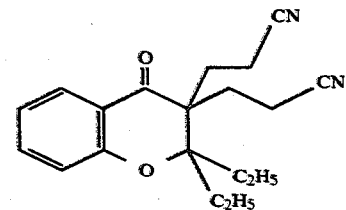 | Oil/$n_D^{25}$ = 1.5516 |

-continued
| Example | | |
|---|---|---|
| (31) | 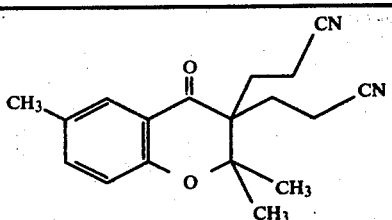 | Melting point 102–4° |
| (32) | 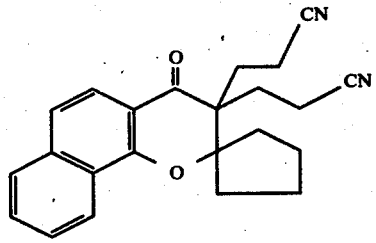 | Melting point 165–7° |
| (33) | 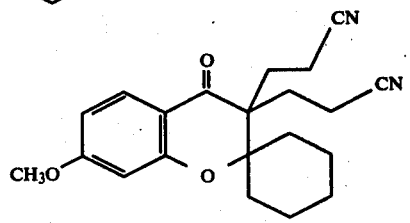 | Melting point 193–6° |
| (34) | 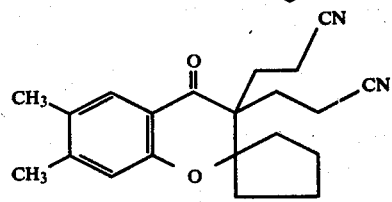 | Melting point 113–5° |
| (35) | 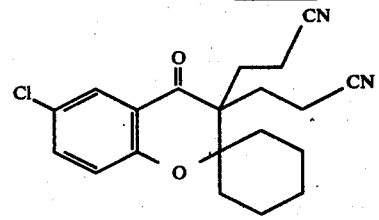 | Melting point 128–30° |
| (36) | 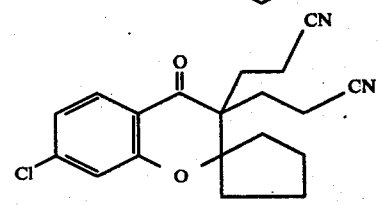 | Melting point 54–5° |
| (37) | 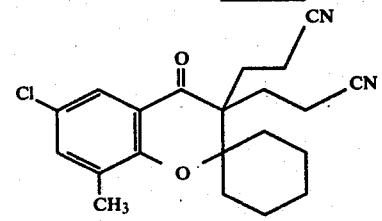 | Melting point 126–7° |
| (38) | 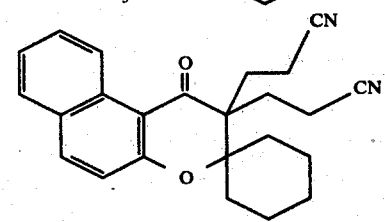 | Melting point 182–4 |

-continued
| Example | | |
|---|---|---|
| (39) | 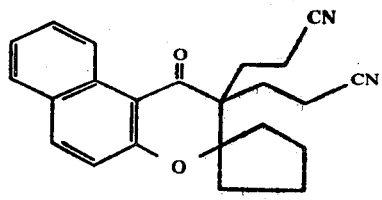 | Melting point 122–4° |
| (40) | 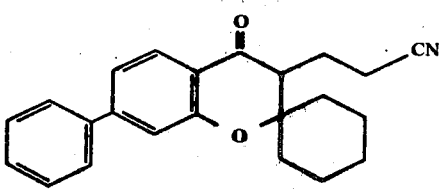 | Melting point 96–7° |
| (41) | 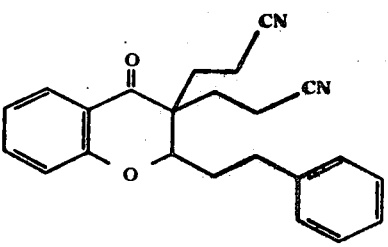 | Melting point 97–100° |
| (42) | 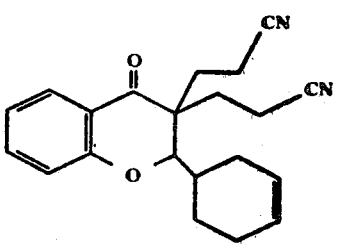 | Melting point 123–5° |
| (43) | 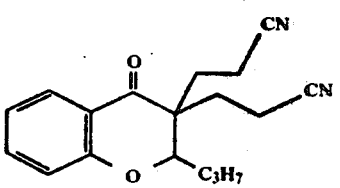 | Melting point 103–4° |
| (44) | 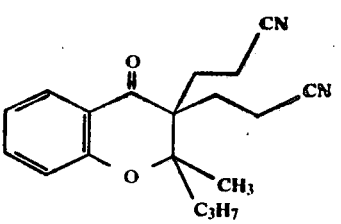 | Oil, $n_D^{25} = 1.5482$ |
| (45) | 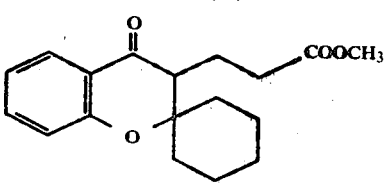 | Boiling point 200–20°/0.3 |
| (46) | 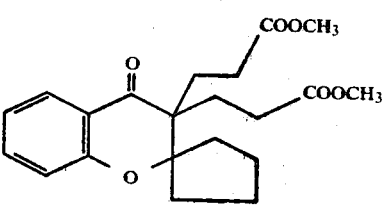 | Resin |

-continued
| Example | | |
|---|---|---|
| (47) | 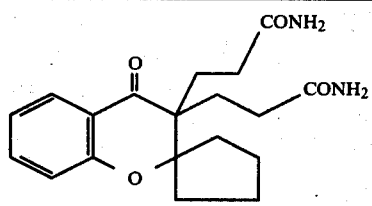 | Melting point 194–6° |
| (48) | 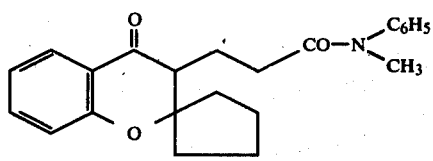 | Melting point 80–2° |
| (49) | 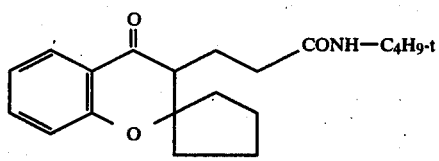 | Melting point 156–8° |
| (50) | 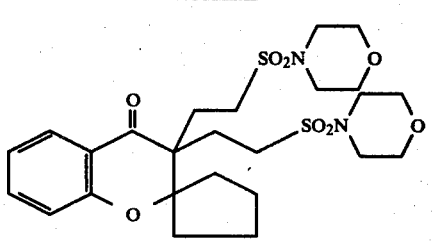 | Melting point 191–2° |
| (51) | 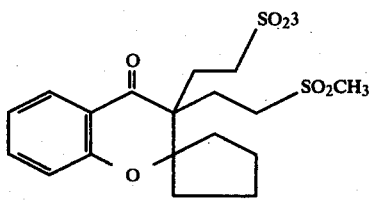 | Melting point 183–4° |
| (52) | 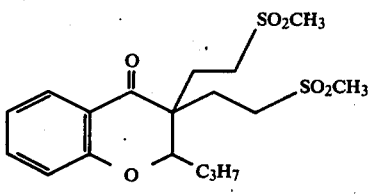 | Melting point 160–1° |
| (53) | 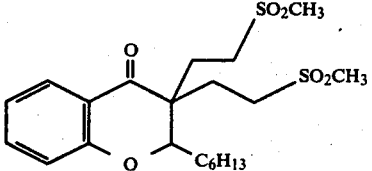 | Melting point 137–8° |
| (54) | 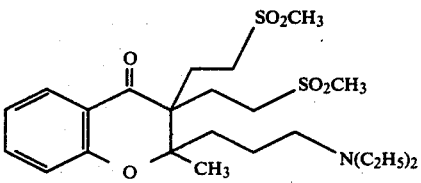 | Melting point 140–2° |
| (55) | 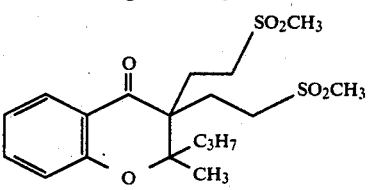 | Melting point 166–8° |

-continued
| Example | | |
|---|---|---|
| (56) | 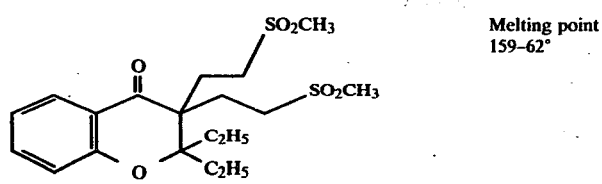 | Melting point 159-62° |
| (57) | 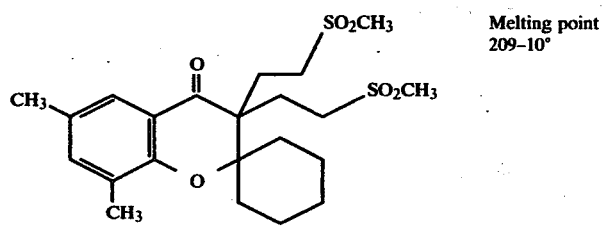 | Melting point 209-10° |
| (58) | 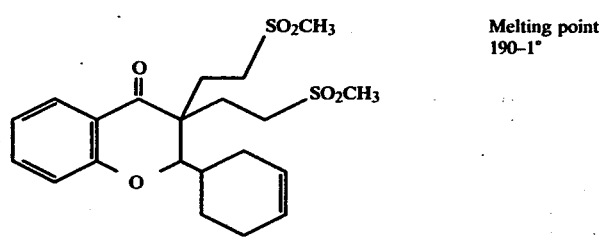 | Melting point 190-1° |
| (59) | 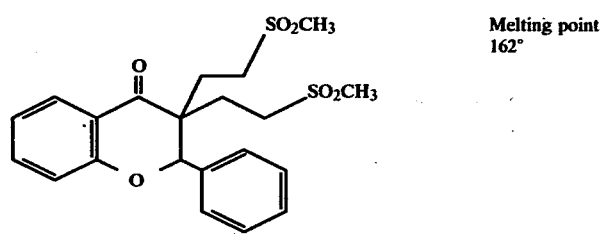 | Melting point 162° |
| (60) | 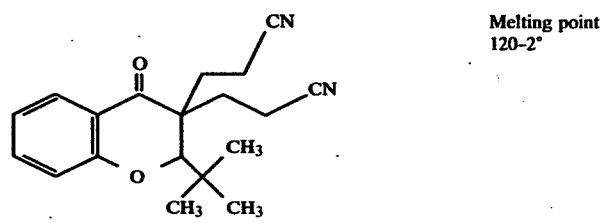 | Melting point 120-2° |
| (61) | 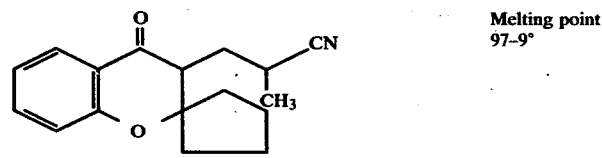 | Melting point 97-9° |
| (62) | 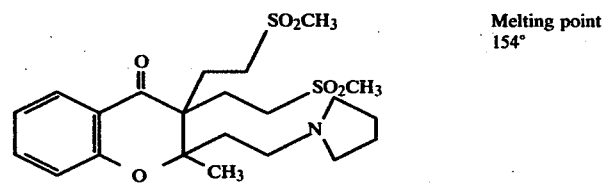 | Melting point 154° |
| (63) | 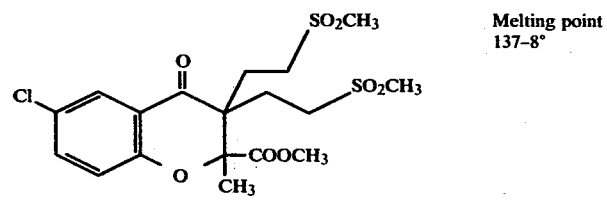 | Melting point 137-8° |

| Example | | |
|---|---|---|
| (64) | 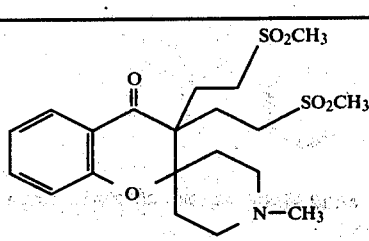 | Melting point 207–9° |
| (65) | 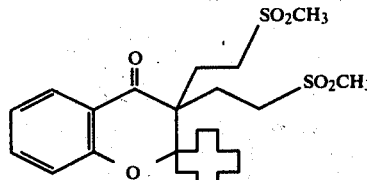 | Melting point 176–8° |
| (66) | 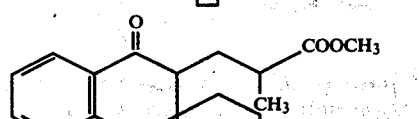 | Boiling point 156–8°/0.15 |
| (67) | 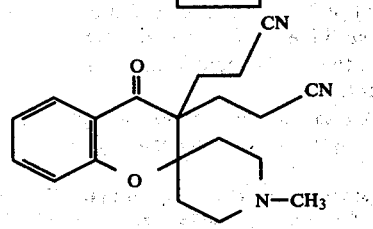 | Melting point 122–3° |

Among the new chromanone salts of the invention, those salts that are pharmaceutically acceptable are particularly important and are preferred.

The new free chromanones of the general formula I and their salts can be interconverted in any suitable manner; methods for such interconversion are known in the art.

The present invention also comprises pharmaceutically acceptable bioprecursors of the active compounds of the present invention.

For the purposes of this Specification the term 'pharmaceutically acceptable bioprecursor' of an active compound of the invention means a compound having a structural formula different from the active compound but which nonetheless, upon administration to an animal or human being is converted in the patient's body to the active compound.

What is claimed is:

1. A compound of the general formula

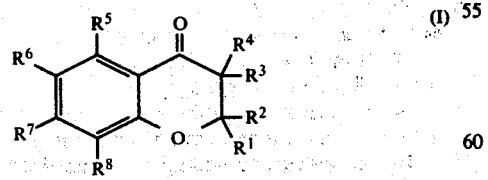

or a salt thereof
in which $R^1$ and $R^2$ are identical or different and each denotes a
  hydrogen atom or alkyl having up to 18 carbon atoms,
  alkenyl having up to 18 carbon atoms, cycloalkyl or cycloalkenyl having 3 to 18 carbon atoms, aryl, aralkyl having 7 to 18 carbon atoms, alkoxycarbonyl having 2 to 7 carbon atoms, carboxyl, dialkylaminoalkyl having 1 to 6 carbon atoms in each alkyl part, or in which $R^1$ and $R^2$, together with the carbon between them, form a 3 to 12-membered carbocyclic or 5 to 12 membered O, N or S heterocyclic ring,
$R^3$ denotes a radical of the general formula

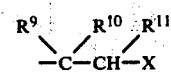

in which $R^9$, $R^{10}$ and $R^{11}$ are identical or different and denote hydrogen or alkyl having 1 to 4 carbon atoms, aminocarbonyl or an alkanoyl group having 1 to 6 carbon atoms, and
X denotes a cyano or nitro group, or a radical of the general formula $COR^{12}$, $SO_2$—$R^{12}$ or $PO(R^{12})_2$, in which
$R^{12}$ denotes a hydrogen atom or a hydroxyl, alkyl having 1 to 12 carbon atoms, phenyl or naphthyl, benzyl, phenylethyl, phenylpropyl, phenylbutyl, naphthylmethyl or naphthylethyl, alkoxy having 1 to 4 carbon atoms, amino, alkylamino having 1 to 4 carbon atoms, alkenylamino having 2 to 4 carbon atoms, phenylamino or dialkylamino having 1 to 4 carbon atoms in each alkyl group,
$R^4$ denotes a hydrogen atom or denotes any of the radicals given for $R^3$, and
$R^5$, $R^6$, $R^7$ and $R^8$ are identical or different and denote a hydrogen or halogen atom or a hydroxyl, nitro, cyano, carboxyl, alkyl having 1 to 4 carbon atoms, cycloalkyl having 5 to 6 carbon atoms, phenyl, naphthyl, benzyl, phenylethyl, phenylpropyl, phenylbutyl, naphthylmethyl or naphthylethyl, alkoxy, alkoxycarbonyl or dialkylamino group in which each alkyl or alkoxy group has 1 to 4 carbon atoms, with the proviso that $R^1$ and $R^9$ may not simultaneously denote phenyl if X denotes CO—$C_6H_5$.

2. Compounds according to claim 1, in which $R^1$ and $R^2$ have the same meanings as in claim 1, $R^3$ denotes a radical of the general formula

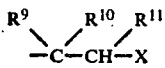

in which $R^9$, $R^{10}$ and $R^{11}$ are identical or different and denote a hydrogen atom or a $C_1$ to $C_4$ alkyl group, $R^4$ denotes a hydrogen atom or has the same meaning as $R^3$, $R^5$, $R^6$, $R^7$ and $R^8$ are identical or different and denote a hydrogen or halogen atom or a $C_1$ to $C_4$-alkyl, hydroxyl or $C_1$ to $C_4$-alkoxy and X denotes a cyano group or a radical of the general formula $COR^{12}$ or $SO_2R^{12}$,
in which $R^{12}$ denotes a $C_1$ to $C_{12}$ alkyl, phenyl or naphthyl radical.

3. Compound according to claim 1, characterised by the formula

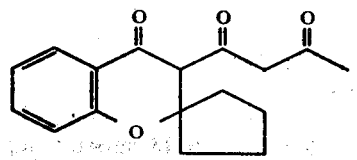

4. Compound according to claim 1, characterised by the formula

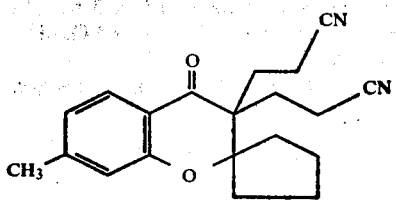

5. Compound according to claim 1, characterised by the formula

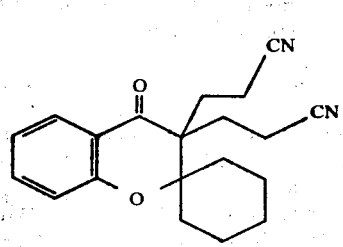

6. Compound according to claim 1, characterised by the formula

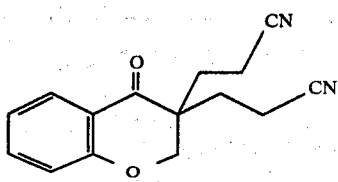

7. Compound according to claim 1, characterised by the formula

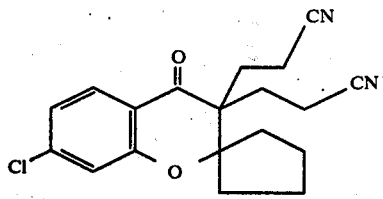

8. A pharmaceutical composition comprising an anticholesteroloemia effective amount of, as an active ingredient, a compound according to claim 1 in admixture with a solid or liquefied gaseous diluent or in admixture with a liquid diluent other than a solvent of a molecular weight less than 200 except in the presence of a surface-active agent.

9. A pharmaceutical composition of claim 8 in the form of a sterile or physiologically isotonic aqueous solution.

10. A composition according to claim 8 or 9 containing from 0.5 to 95% by weight of the said active ingredient.

11. A medicament in dosage unit form comprising an anticholesterolaemia effective amount of a compound according to claim 1 together with an inert pharmaceutical carrier.

12. A medicament of claim 11 in the form of tablets, pills, dragees, capsules, ampoules or suppositories.

13. A method of combating cholesterolaemia in warm-blooded animals which comprises administering to the said animals an anticholesterolaemia effective amount of an active compound according to claim 1 either alone or in admixture with a diluent or in the form of a medicament.

14. A method according to claim 13 in which the active compound is administered in an amount of 0.05 to 500 mg per kg body weight per day, divided into 1 to 6 administrations.

15. A method according to claim 13 in which the active compound is administered in an amount of 0.5 mg to 200 mg/per kg body weight per day, divided into 1 to 6 administrations.

16. A method according to claims 13, 14 or 15 in which the animals are ruminants.

17. A method according to claims 13, 14 or 15 in which the animals are pigs.

18. A method according to claims 13, 14 or 15 in which the animals are chicks or broilers.

19. A method according to claim 13 in which the active compound is administered orally.

* * * * *